US007838252B2

(12) United States Patent
Cohen et al.

(10) Patent No.: US 7,838,252 B2
(45) Date of Patent: Nov. 23, 2010

(54) METHODS AND COMPOSITIONS FOR TREATING A SUBJECT HAVING AN ANTHRAX TOXIN MEDIATED CONDITION

(75) Inventors: Stanley N. Cohen, Stanford, CA (US); Wensheng Wei, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 250 days.

(21) Appl. No.: 11/356,740

(22) Filed: Feb. 16, 2006

(65) Prior Publication Data
US 2006/0257892 A1 Nov. 16, 2006

Related U.S. Application Data

(60) Provisional application No. 60/654,182, filed on Feb. 18, 2005, provisional application No. 60/654,658, filed on Feb. 17, 2005.

(51) Int. Cl.
*C12Q 1/68* (2006.01)
*G01N 33/53* (2006.01)
*G01N 33/567* (2006.01)

(52) U.S. Cl. .............. 435/7.2; 424/130.1; 424/143.1; 424/141.1; 424/152.1; 435/7.21

(58) Field of Classification Search ............ None
See application file for complete search history.

(56) References Cited

U.S. PATENT DOCUMENTS

| 6,436,933 | B1 | 8/2002 | Rideout et al. | |
|---|---|---|---|---|
| 7,138,417 | B2* | 11/2006 | Staehle et al. | 514/349 |
| 7,169,559 | B2* | 1/2007 | Reid et al. | 435/6 |
| 7,282,580 | B2* | 10/2007 | Singh et al. | 536/23.7 |
| 7,456,264 | B2* | 11/2008 | Keler et al. | 530/388.4 |
| 2002/0034512 | A1* | 3/2002 | Ivins et al. | 424/184.1 |
| 2003/0144193 | A1* | 7/2003 | Rottman et al. | 514/12 |
| 2003/0165501 | A1* | 9/2003 | DeAlmeida et al. | 424/145.1 |
| 2003/0235818 | A1* | 12/2003 | Katritch et al. | 435/5 |

(Continued)

FOREIGN PATENT DOCUMENTS

WO 2003/076568 * 9/2003

(Continued)

OTHER PUBLICATIONS

Lacy, D. Borden et al, PNAS, Sep. 7, 2004, vol. 101(36), pp. 13147-13151.*

(Continued)

*Primary Examiner*—Robert B Mondesi
*Assistant Examiner*—Ginny Portner
(74) *Attorney, Agent, or Firm*—Bozicevic, Field & Francis LLP; David C. Scherer; Bret E. Field

(57) ABSTRACT

Methods and compositions for treating a subject for an anthrax toxin mediated disease condition are provided. Aspects of the subject methods include administering to a subject an effective amount of an agent that inhibits cellular internalization of an anthrax toxin, e.g., such as a LRP6 modulatory agent. Also provided are active agents suitable for use in the subject methods, as well as pharmaceutical preparations thereof.

7 Claims, 10 Drawing Sheets

U.S. PATENT DOCUMENTS

| | | | |
|---|---|---|---|
| 2004/0014209 A1* | 1/2004 | Lassar et al. | 435/366 |
| 2004/0023356 A1* | 2/2004 | Krumlauf et al. | 435/226 |
| 2004/0038860 A1* | 2/2004 | Allen et al. | 514/2 |
| 2004/0092454 A1* | 5/2004 | Schadt et al. | 514/19 |
| 2004/0142877 A1* | 7/2004 | Schadt et al. | 514/19 |
| 2004/0171559 A1* | 9/2004 | Weissman et al. | 514/27 |
| 2004/0235166 A1* | 11/2004 | Prockop et al. | 435/377 |
| 2004/0253249 A1* | 12/2004 | Rudnic et al. | 424/184.1 |
| 2004/0258699 A1* | 12/2004 | Bowdish et al. | 424/184.1 |
| 2005/0031625 A1* | 2/2005 | Mohamed et al. | 424/164.1 |
| 2005/0042634 A1* | 2/2005 | Jones et al. | 435/6 |
| 2005/0153902 A1* | 7/2005 | Staehle et al. | 514/19 |
| 2005/0250692 A1* | 11/2005 | Huang | 514/12 |
| 2005/0261181 A1* | 11/2005 | Wu et al. | 514/12 |
| 2005/0287149 A1* | 12/2005 | Keler et al. | 424/164.1 |
| 2006/0083746 A1* | 4/2006 | Young et al. | 424/164.1 |
| 2006/0110801 A1* | 5/2006 | Young et al. | 435/69.3 |
| 2006/0148716 A1* | 7/2006 | Jonczyk et al. | 514/16 |
| 2006/0217298 A1* | 9/2006 | Srivastava | 514/12 |
| 2006/0257892 A1* | 11/2006 | Cohen et al. | 435/6 |
| 2006/0258842 A1* | 11/2006 | Groen et al. | 530/350 |
| 2006/0263791 A1* | 11/2006 | Moon et al. | 435/6 |
| 2007/0077553 A1* | 4/2007 | Bentwich | 435/5 |
| 2007/0111253 A1* | 5/2007 | Harada et al. | 435/7.1 |
| 2007/0292444 A1* | 12/2007 | Krumlauf et al. | 424/179.1 |
| 2008/0020407 A1* | 1/2008 | Jamieson et al. | 435/723 |
| 2008/0044901 A1* | 2/2008 | Sasai et al. | 435/377 |
| 2008/0299148 A1* | 12/2008 | Young et al. | 424/199.1 |

FOREIGN PATENT DOCUMENTS

| | | | |
|---|---|---|---|
| WO | 2004/053069 | * | 6/2004 |

OTHER PUBLICATIONS

Bann et al, Cell, vol. 124, Mar. 24, 2006, pp. 119-121, LRP6 Holes the Key to the Entry of Anthrax toxin.*
Young, John J. e tal, PLoS Pathogens, Mar. 2007, vol. 3(3), e27, pp. 1-9, LRP5 and LRP6 are not required for Protective antigen-mediated Internalization or Lethality of Anthrax Lethal Toxin.*
Mourez et al, Nov. 2003, PNAS (USA), vol. 100(24), pp. 13803-138-8, Mapping Dominant Negative mutants of Anthrax Protective Antigen by scanning mutagenesis.*
Abrami, L et al, The Journal of Cell Biology, vol. 160(3), pp. 321-328, Feb. 3, 2003, Anthrax toxin triggers endocytosis of its receptor via a lipid raft-mediated clathrin-dependent process.*
Wei, W et al 2006, Cell, vol. 124, pp. 1141-1154, Mar. 24, 2006, The LDL Receptor-related protein LRP6 mediates internalization and lethality of Anthrax toxin.*
Singh, Y et al, The Journal of Biological Chemistry, vol. 276(25), Jun. 22, 2001, pp. 22090-22094, A Dominant Negative Mutant of *Bacillus anthracis* Protective antigen inhibits Anthrax toxin action in Vivo.*
Young, J.J. et al, PLOS Pathogens, Mar. 2007, vol. 3(3e27), pp. 0001-0009.*
Strickland, DK et al, FASEB J., vol. 9, pp. 890-898, 1995, LDL recept0or-related protein: a multiligand receptor for lipoprotein and proteinase catabolism.*
Strickland, DK et al, Trends in Endocrinology and Metabolism, vol. 13(2) Mar. 2002, Diverse roles for the LDL receptor family.*
Mao, B. et al, Nature, vol. 411, May 17, 2001, LDL receptor related protein 6 is a reeptor for Dickkopf proteins, pp. 321-325.*
Davidson, G et al, Development, vol. 129, pp. 5587-5596, 2002.*
Itasaki. Nobue et al, Development, vol. 130, pp. 4295-4305, 2003.*
Abrami, L et al, J. Cell Biology, vol. 160(3), Feb. 3, 2003, pp. 321-328.*
Rainey et al. "Receptor-Specific Requirements for Anthrax Toxin Delivery into Cells," Proc. Natl. Acad. Sci. (2005) 102(37):13278-13283.
Santelli et al. "Crystal Structureof a Complex Between Anthrax Toxin and its Host Cell Receptor," Nature (2004) 430(19):905-908.
Scobie et al. "Human Capillary Morphogenesis Protein 2 Functions as an Anthrax Toxin Receptor," Proc. Natl. Acad. Sci. (2003) 100(9):5170-5174.
Scobie et al. "Interactions Between Anthrax Toxin Receptors and Protective Antigen," Current Opinion in Microbiology (2005) 8:106-112.
Wei et al. "The LDL Receptor-Related Protein LRP6 Mediates Internalization and Lethality of Anthrax Toxin," Cell(2006) 124:1141-1154.

* cited by examiner

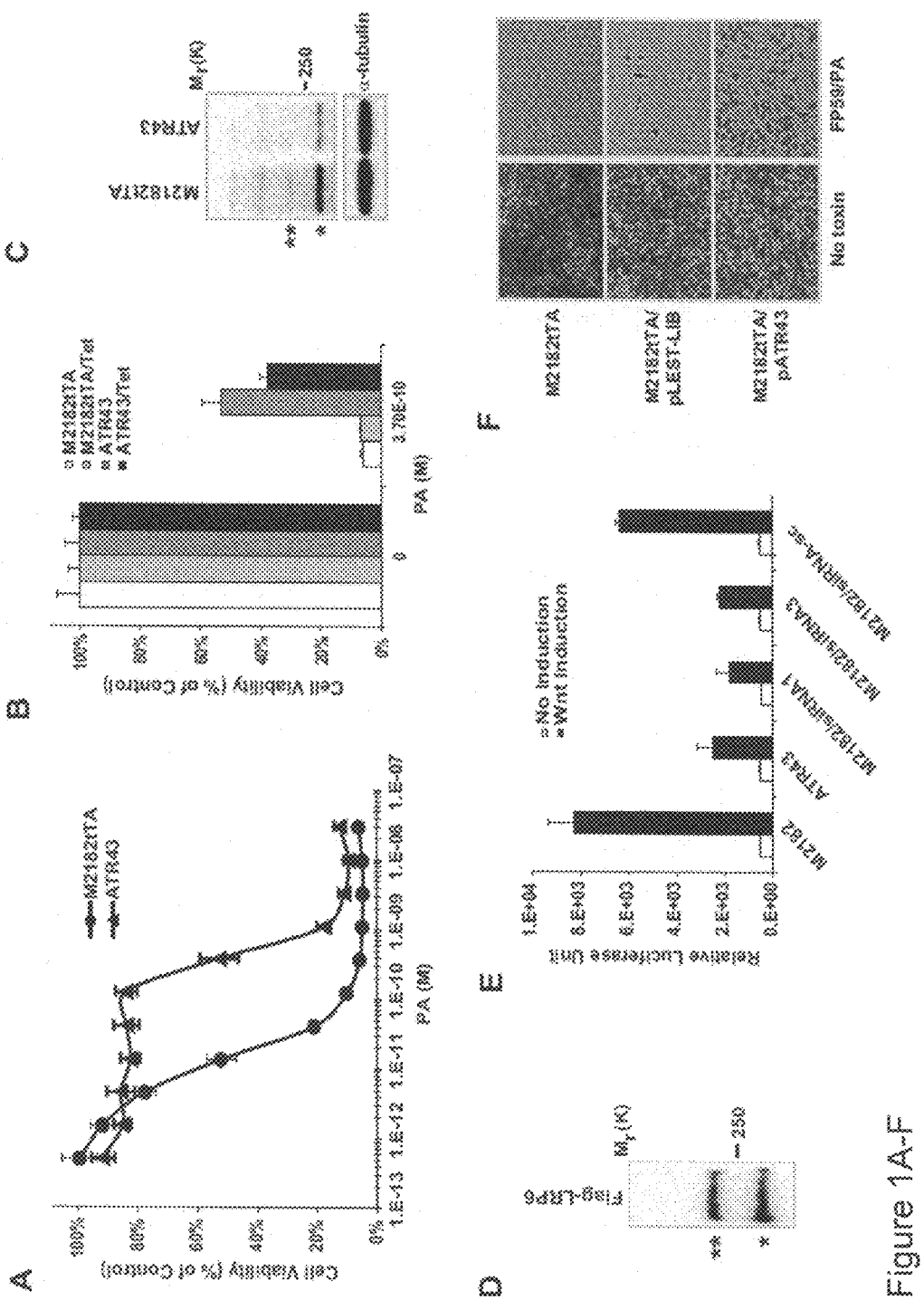
Figure 1A-F

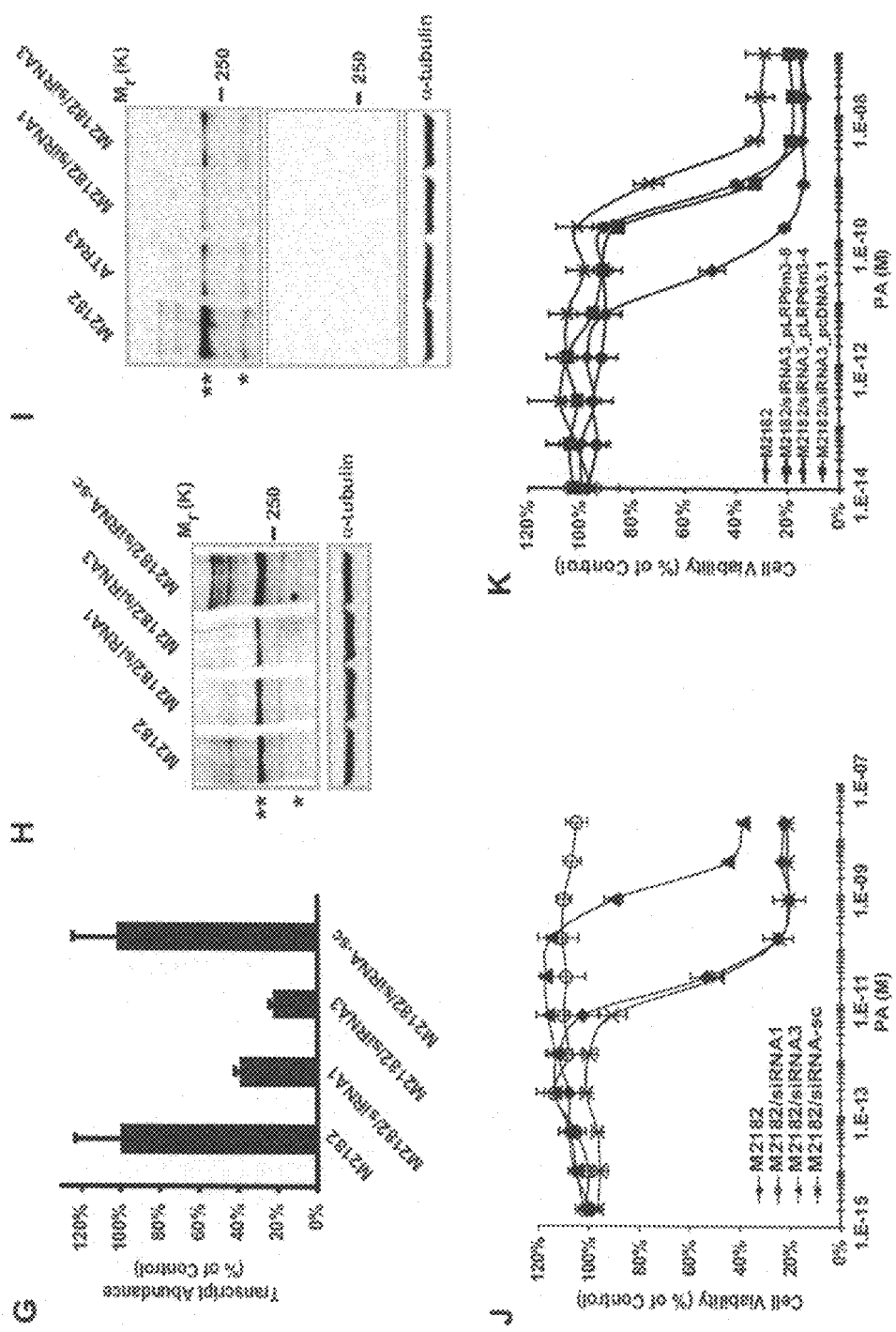
Figure 1G-K

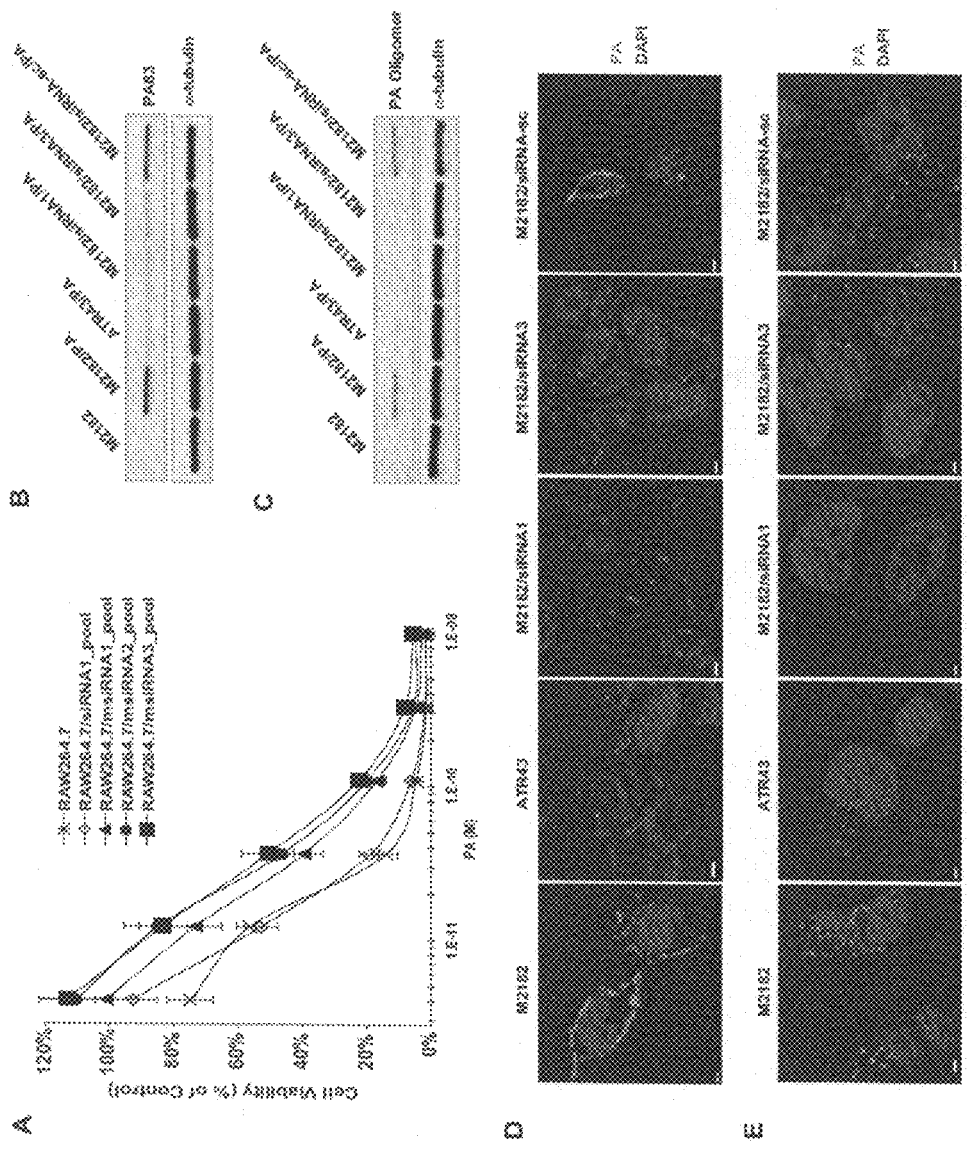
Figure 2A-E

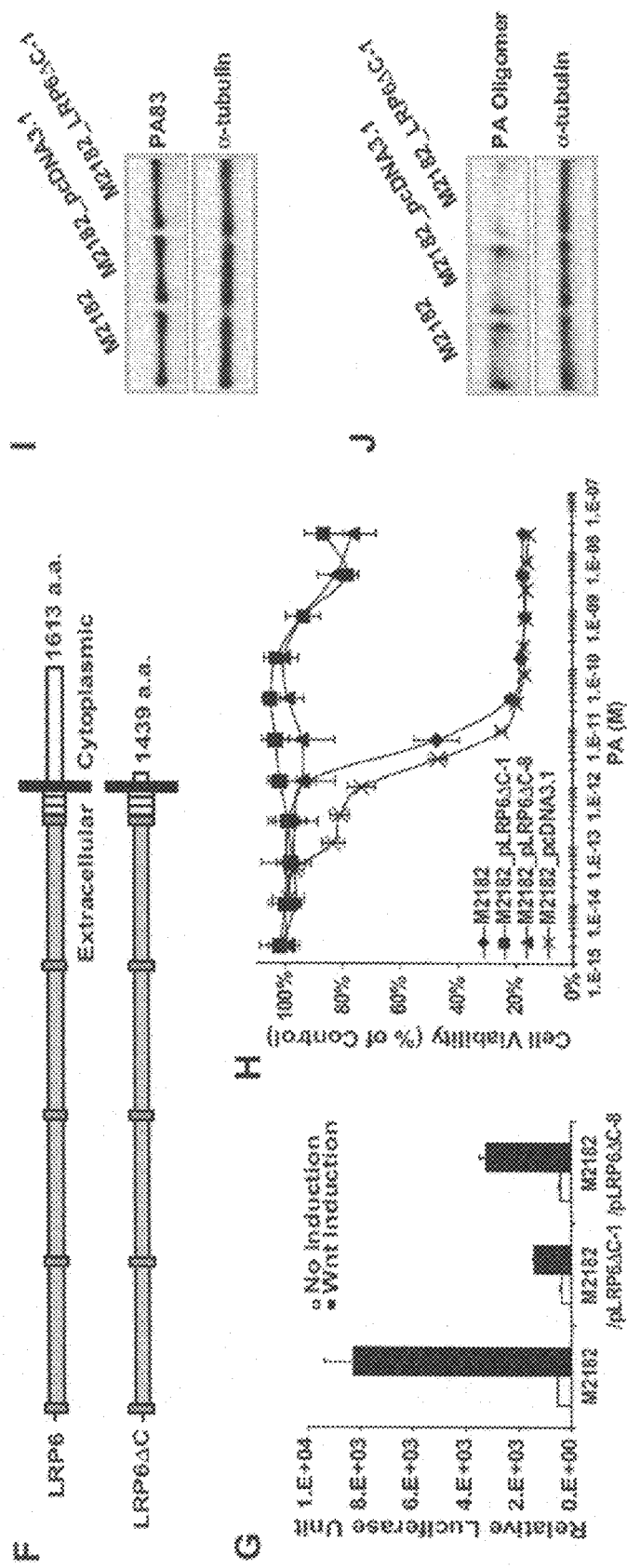
Figure 2F-J

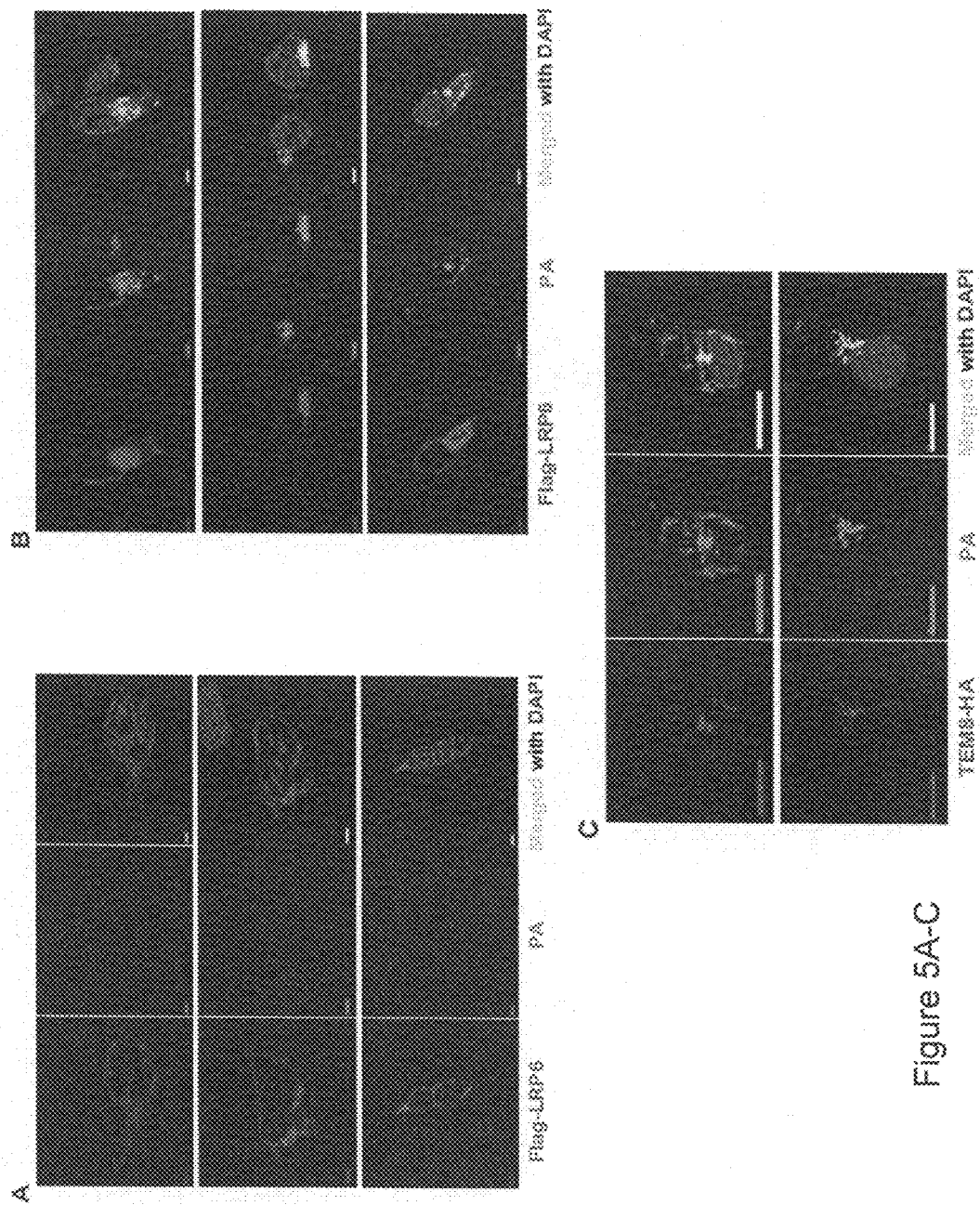
Figure 5A-C

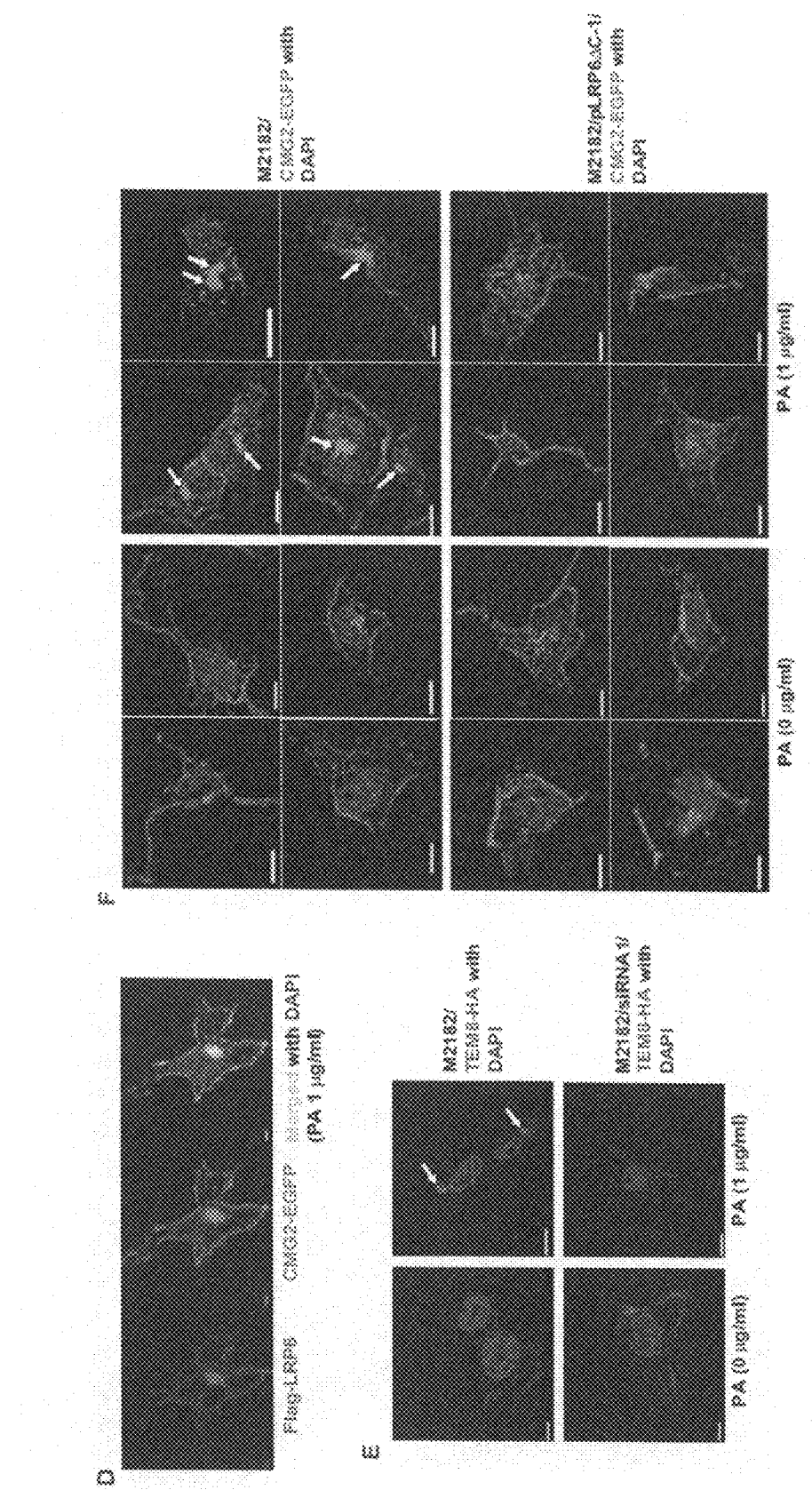
Figure 5D-F

Figure 7

```
                        SEQUENCE LISTING

<160> NUMBER OF SEQ ID NOS: 16

<210> SEQ ID NO 1
<211> LENGTH: 28
<212> TYPE: DNA
<213> ORGANISM: homo sapiens

<400> SEQUENCE: 1
cggatccaag atgggggccg tcctgagg                                         28

<210> SEQ ID NO 2
<211> LENGTH: 62
<212> TYPE: DNA
<213> ORGANISM: homo sapiens

<400> SEQUENCE: 2
tagcggccgc tacagatctt cttcagaaat aagtttttgt tccattcctg gaagagatcc      60
tg                                                                     62

<210> SEQ ID NO 3
<211> LENGTH: 21
<212> TYPE: DNA
<213> ORGANISM: homo sapiens

<400> SEQUENCE: 3
ggagatgcca aaacagacaa g                                                21

<210> SEQ ID NO 4
<211> LENGTH: 21
<212> TYPE: DNA
<213> ORGANISM: homo sapiens
```

-continued

<400> SEQUENCE: 4
ggagatgcca aaacagacaa g                                    21

<210> SEQ ID NO 5
<211> LENGTH: 23
<212> TYPE: DNA
<213> ORGANISM: homo sapiens

<400> SEQUENCE: 5
gaggcactct tccagccttc ctt                                  23

<210> SEQ ID NO 6
<211> LENGTH: 22
<212> TYPE: DNA
<213> ORGANISM: homo sapiens

<400> SEQUENCE: 6
gcgtacaggt ctttgcggat gt                                   22

<210> SEQ ID NO 7
<211> LENGTH: 20
<212> TYPE: PRT
<213> ORGANISM: homo sapiens

<400> SEQUENCE: 7

Asn Phe Ile His Lys Ser Asn Leu Asp Gly Thr Asn Arg Gln Ala Val
 1               5                  10                  15

Val Lys Gly Ser
            20

<210> SEQ ID NO 8
<211> LENGTH: 20
<212> TYPE: PRT
<213> ORGANISM: homo sapiens

<400> SEQUENCE: 8

Asn Phe Ile His Lys Ser Asn Leu Asp Gly Thr Asn Arg Gln Ala Val
 1               5                  10                  15

Val Lys Gly Ser
            20

<210> SEQ ID NO 9
<211> LENGTH: 19
<212> TYPE: DNA
<213> ORGANISM: homo sapiens

<400> SEQUENCE: 9
tgctacgatt gtagttgga                                       19

<210> SEQ ID NO 10
<211> LENGTH: 19
<212> TYPE: DNA
<213> ORGANISM: homo sapiens

<400> SEQUENCE: 10
cgaatcgaat tgaggtgtc                                       19

<210> SEQ ID NO 11
<211> LENGTH: 19
<212> TYPE: DNA
<213> ORGANISM: homo sapiens

<400> SEQUENCE: 11

```
tgtctcgagg taaatcaat                                                    19

<210> SEQ ID NO 12
<211> LENGTH: 19
<212> TYPE: DNA
<213> ORGANISM: homo sapiens

<400> SEQUENCE: 12
gagaatgcaa cgattgtag                                                    19

<210> SEQ ID NO 13
<211> LENGTH: 19
<212> TYPE: DNA
<213> ORGANISM: homo sapiens

<400> SEQUENCE: 13
gtgctttgtt taattgatc                                                    19

<210> SEQ ID NO 14
<211> LENGTH: 19
<212> TYPE: DNA
<213> ORGANISM: homo sapiens

<400> SEQUENCE: 14
atacacatct ggttgagat                                                    19

<210> SEQ ID NO 15
<211> LENGTH: 11
<212> TYPE: PRT
<213> ORGANISM: homo sapiens

<400> SEQUENCE: 15

Asp Thr Gly Thr Asp Arg Ile Glu Val Thr Arg
 1               5                  10

<210> SEQ ID NO 16
<211> LENGTH: 4
<212> TYPE: PRT
<213> ORGANISM: homo sapiens

<400> SEQUENCE: 16

Tyr Trp Thr Asp
 1
```

METHODS AND COMPOSITIONS FOR TREATING A SUBJECT HAVING AN ANTHRAX TOXIN MEDIATED CONDITION

CROSS-REFERENCE TO RELATED APPLICATIONS

Pursuant to 35 U.S.C. §119 (e), this application claims priority to the filing date of U.S. Provisional Patent Application Ser. No. 60/654,182 filed on Feb. 18, 2005 and to the filing date of U.S. Provisional Application Ser. No. 60/654,658 filed on Feb. 17, 2005; the disclosures of which applications are herein incorporated by reference.

FEDERALLY-SPONSORED RESEARCH OR DEVELOPMENT

This invention was made with Government support under contract N65236-99-1-5425 awarded by the Defense Advanced Research Projects Agency. The Government has certain rights in this invention.

BACKGROUND

Anthrax is a lethal disease of humans and other animals caused by the gram-positive spore-forming eubacterium, *Bacillus anthracis*. While this disease has long been endemic to most countries, its incidence in human populations largely has been controlled. However, the worldwide prevalence of *B. anthracis* and the ease of culturing this lethal microbe have focused much recent attention on anthrax as an agent of bioterrorism.

The virulence of *B. anthracis* infection is due to the cellular effects of separate complexes formed by interaction of a carrier protein, protective antigen (PA, 83 kDa) with lethal factor (LF, 90 kDa) or edema factor (EF, 89 kDa). During infection by *B. anthracis*, PA binds to receptors on the surface of macrophages and is cleaved by the protease furin, releasing a 20 kDa fragment and enabling the residual receptor-bound C-terminal 63 kDa PA peptide fragment (PA63) to form heptamers and interact with LF or EF. After entering target cells by endocytosis, PA/LF and PA/EF complexes translocate across the endosomal membrane into the cytosol where they dissociate, allowing LF and EF to exert their toxic effects.

LF is a Zn++ protease that cleaves the amino terminus of all MAPK kinases and consequently is responsible for anthrax lethality. EF is a calmodulin-dependent adenylate cyclase that elevates intracellular levels of cAMP, producing profound edema as a typical clinical symptom and impairing the immune response to infection.

SUMMARY

Methods and compositions for treating a subject for an anthrax toxin mediated disease condition are provided. Aspects of the subject methods include administering to a subject an effective amount of an agent that inhibits cellular internalization of anthrax toxin, such as a LRP6 modulatory agent. Also provided are active agents suitable for use in the subject methods, as well as pharmaceutical preparations thereof.

BRIEF DESCRIPTION OF THE FIGURES

FIGS. 1A to 1K. Evidence That LRP6 Deficiency Mitigates Toxicity to PA+FP59. (A) Cytotoxicity of the naïve M2182tTA and clone ATR43 to PA/FP59. The MTT assay was performed as described in Experimental Procedures. The values shown represent the mean and standard deviation, as defined by error bars in this and other figures. (B) Effect of tetracycline on resistance of ATR43 to PA/FP59. Cells were seeded at a concentration of $5 \times 10^3$ cells/well (96-well plate) with or without tetracycline (Tet, 1 µg/ml), and treated with PA (30 ng/ml, or $3.7 \times 10^{-10}$ M) plus FP59 (50 ng/ml) for 2 days before being assayed by MTT. (C) Immunoblot analysis of lysates from naïve M2182tTA and mutant clone ATR43 cells using murine monoclonal antibody directed against human LRP5/6. α-tubulin bands were measured in Western blots as internal controls. In SDS-PAGE gels LRP6 appeared in both monomer (*) and dimer (**) forms in the presence of the reducing agent, β-mercaptoethanol (β-ME). (D) Confirmation of the molecular nature of both monomer (*) and dimer (**) bands of LRP6 proteins. N-terminal-tagged Flag-LRP6 was transfected into 293T cell, and the expressing lysates from transiently transfected cells were electrophoresed under SDS-PAGE conditions in the presence of β-ME were probed in immunoblots using anti-Flag monoclonal antibody. (E) Effect of LRP6 deficiency on cellular response to Wnt activation. The data shown are the summed results of three independent experiments. (F) Effect of LRP6 deficiency induced in naïve cells. The EST identified in the ATR43 mutant was re-introduced into pLEST in the antisense orientation. Pooled populations of infected M2182tTA clones in 6-well plates were treated with PA/FP59, and photographed by microscopy at a magnification of 100 X. M2182/pLEST-LIB refers to EST library in M2182 cells serving as a control. The values represent the mean and S.D. (bars). (G) Effect of lrp6-specific siRNA on transcript abundance. lrp6 transcripts were measured by quantitative RT-PCR, normalized to β-actin mRNA. Filled in bars indicate transcript abundance compared with wild type M2182. Each data point represents an average of three repeats. (H-I) Immunoblot assays of lysates of M2182 cells expressing siRNAs directed against lrp6 transcripts. Antibodies used for detection were rabbit polyclonal antibody H300 (H) against human LRP6 protein and murine monoclonal antibody against human LRP5/6 (I). Anti-α-tubulin antibody was used to calibrate loading of lysates on gels. Both monomer (*) and dimer (**) forms of LRP6 protein bands are shown. Antibody specificity was confirmed by blotting the same membrane using antibody that had been preabsorbed with an excess of the peptide used as the immunogen (I, middle). (J-K) Cytotoxicity of PA+FP59 in M2182 cells treated with siRNAs (J), and in M2182/siRNA3 cells expressing LRP6 protein (K). Cell viability was assessed as described in FIG. 1A. Two individual M2182/siRNA3 clones expressing the mutant LRP6 m3 construct were subjected to the PA+FP59 toxin assay (K). A clone containing the expression vector alone (pcDNA3.1) was included as a control for effects of the extended procedure per se on siRNA modulated interference with toxicity.

FIGS. 2A to 2J: Effect of LRP6 on PA Binding and Internalization. (A) Effect of LRP6 deficiency on mouse macrophage sensitivity to PA+LF. pLENTI-SUPER constructs expressing siRNAs directed against murine lrp6 transcripts were introduced into RAW264.7 cells by transfection, and the cells acquiring the vector were selected by blasticidin and pooled for cytotoxicity assays. Controls were RAW264.7 cells expressing human lrp6 siRNA1 which shares no homology with the mouse lrp6 sequence, and the naïve RAW264.7 cells not subjected to transfection. Cells at $1 \times 10^3$ cells per well in 96-well plates were treated with serially diluted PA and 500 ng/ml of LF for 2 days. Cell viability was assessed using MTT assay as described in FIG. 1A. This experiment was repeated five times with separate transfection assays and similar quantitative differences in experimental and control samples were observed. (B-C) Western blot analysis of bound (B) and internalized (C) PA in different cells was conducted following the protocol as described in Experimental Procedures. PA83 is the full-length form of PA (83 kDa), and the oligomer represents the heptamer of PA63. α-tubulin abundance was measured as an internal control. (D) For PA binding assay, cells were incubated with Fluor 488-labelled PA for one hr at 4° C. before being examined by deconvolution microscopy following the protocol described in Experimental Procedures. The scale bar=2.8μ. (E) For PA internalization assays, cells were incubated with Fluor 488-labelled PA (1 μg/ml) for 45 min at 37° C. followed by deconvolution microscopy (scale bar=2.8μ. (F) Schematic structure of dominant-negative mutant LRP6ΔC and wild type LRP6 proteins. LRP6ΔC was generated by deleting amino acid residues from 1440 onward (Tamai et al., 2000), as described in Experimental Procedures. (G) Effect of LRP6ΔC production on cellular response to Wnt activation. Luciferase reporter gene assay was carried out as in FIG. 1E. The data shown are the averaged results of three independent experiments. (H) Cytotoxicity assay of M2182 expressing LRP6ΔC, pLRP6ΔC-1 and pLRP6ΔC-8. Cell viability was assessed as described in FIG. 1A. (I and J) Western blot analysis of bound (I) and internalized (J) PA in LRP6ΔC mutants. PA binding and internalization assays were carried out as described in Experimental Procedures using anti-PA monoclonal antibodies. α-tubulin was used as an internal control.

FIGS. 5A to 5F: LRP6 Effects on Internalization and Localization of PA and its Receptors. (A-B) Deconvolution microscopy images (three independent image fields for each) showing the co-localization of Flag-LRP6 (red) and PA oligomers (green). M2182 cells were first transfected with Flag-LRP6 2 days prior to fluorescence microscopy. Cells were incubated without PA (panel A) or with Fluor-488-conjugated PA (1 μg/ml) at 37° C. for 45 min (panel B). Flag-LRP6 protein labeled by Fluor-594 (red) is shown in the left panels (A and B). The PA oligomer signal (green) is shown in the middle panels. The right panels show the merged images including DAPI nuclear staining (blue). The scale bar (A and B)=2.8μ. (C) Deconvolution microscopy images showing co-localization of Fluor-594-labelled TEM8-HA (red) with Fluor-488-conjugated PA (1 μg/ml) (green) after cells were incubated with PA (1 μg/ml) for 45 min at 37° C. (scale bar=2.8μ). The top and bottom panels show two independent fields. The right panels show the merged images including DAPI nuclear staining (blue). (D) Deconvolution microscopy images showing the co-localization of Flag-LRP6 (red) and CMG2-EGFP (enhanced green fluorescent protein) after cells were incubated with PA (1 μg/ml) for 45 min at 37° C. (scale bar=2.8μ). (E-F) M2182 cells transfected with TEM8-HA or CMG2-EGFP were first incubated with or without PA (1 μg/ml) at 37° C. for 45 min before deconvolution microscopy. (E) Microscopy images showing aggregates (white arrows) of internalized TEM8-HA (red) in M2182 (top panels) or M2182/siRNA1 cells (bottom panels) in the absence (left panels) or presence (right panels) of PA. The scale bar=5.6μ. (F) Microscopy images showing aggregates (white arrows in four images of top right panels) and localization of CMG2-EGFP (green) in M2182 (top panels) or M2182/pLRP6☐C-1 (bottom panels) without (left panels) or with (right panels) PA. Four independent image fields are used for each panel, and the scale bar=11μ.

Figure 7:
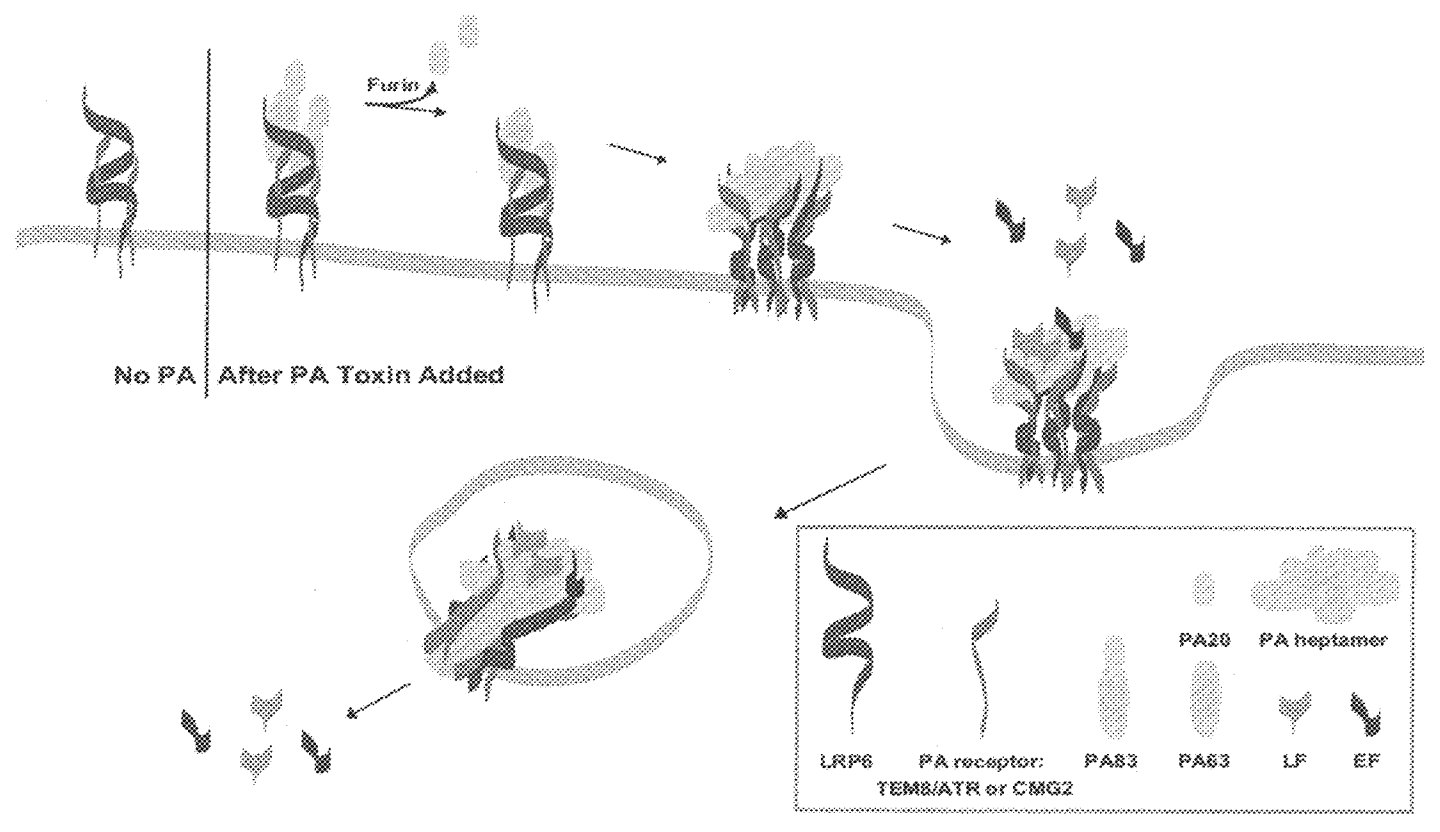

FIG. 7: Model for LRP6-Promoted Internalization of Multicomponent Complex Containing TEM8/ATR and/or CMG2. LRP6 is proposed to act as a co-receptor for PA through its binding to TEM8/ATR and/or CMG2. PA addition triggers the internalization of this complex, which delivers PA and associated toxin molecules into cells.

DETAILED DESCRIPTION

Figure 3:
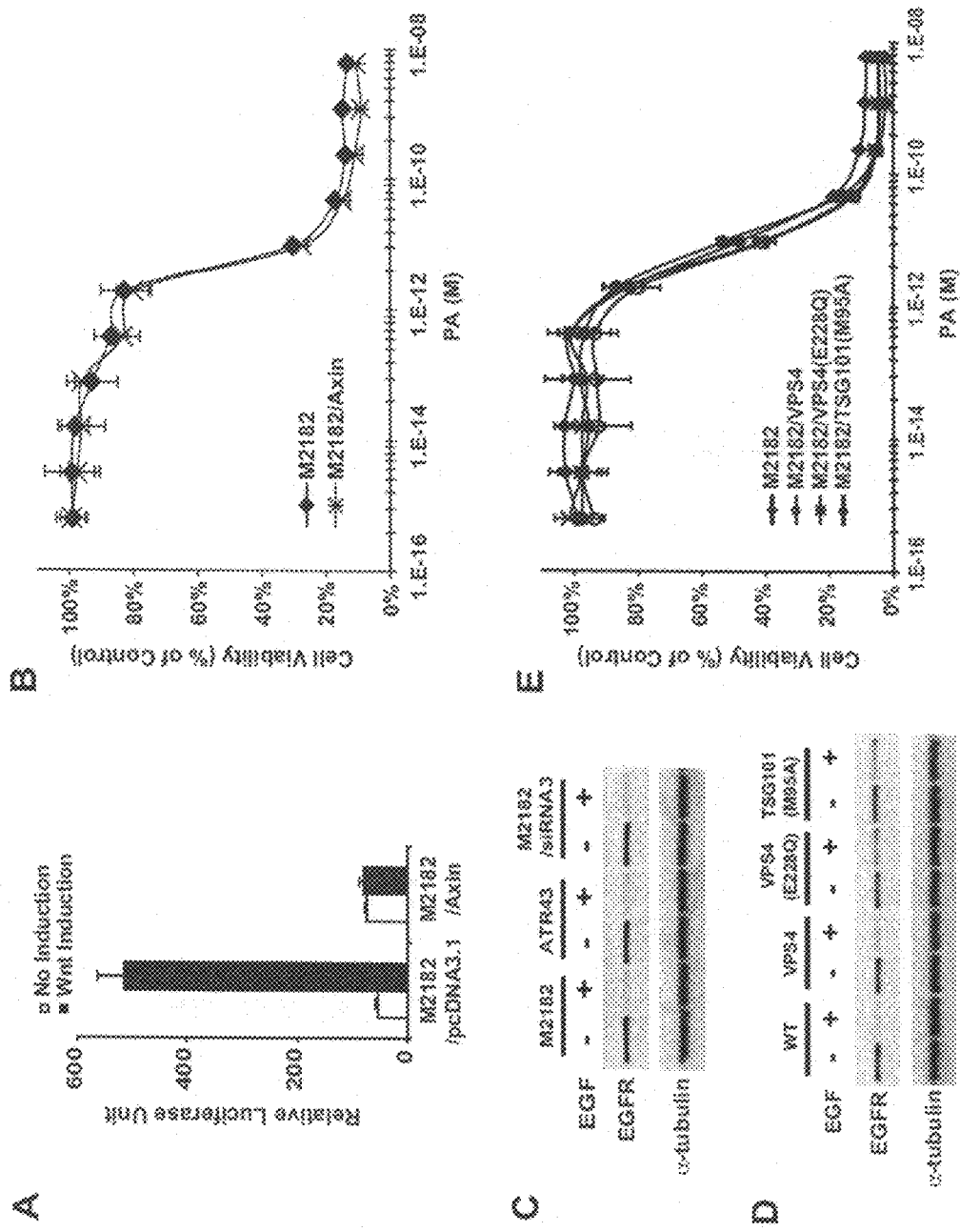
FIGS. 3A to 3E: Specificity of LRP6 Effect on Cell Susceptibility to Anthrax Toxin. (A) Effect of Axin production on cellular response to Wnt activation. Cells in 6-well plates (40-70% confluence) were transiently transfected with the following three DNAs: pcDNA3.1-AxinMyc (2 μg/well) or pcDNA3.1 (2 μg/well); Super8XTOPflash (1 μg/well); and pcDNA-lacZ plasmid (0.1 μg/well). Luciferase reporter gene assay was carried out as in FIG. 1E. The data shown are the averaged results of three independent experiments. (B) Cytotoxicity assay of M2182 expressing Axin. Cells transfected with the Axin expression construct as in FIG. 3A were subjected to the PA/FP59 toxin assay. (C-D) Assay of ligand-induced EGF receptor (EGFR) degradation. (C) Effects of LRP6 mutants on EGFR degradation in M2182 cells and its LRP6 deficient mutants, ATR43 and M2182/siRNA3. (D) Effects of overexpression of VPS4, VPS4 (E228Q) and TSG101 (M95A) on EGF-induced EGFR degradation. M2182 cells were transfected in 6-well plates with pcDNA-EGFR (200 ng/well), along with one of the following: VPS4, VPS4 (E228Q), or TSG101 (M95A) (1 μg/well for each of the three). Assays were performed as described in Experimental Procedures. (E) Cytotoxicity assay of M2182 expressing VPS4, VPS4 (E228Q), or TSG101 (M95A). Cells transfected with different expression constructs, as in FIG. 3D, were subjected to the PA/FP59 toxin assay.

Methods and compositions for treating a subject for an anthrax toxin mediated disease condition are provided. Aspects of the subject methods include administering to a subject an effective amount of an agent that inhibits cellular internalization of an anthrax toxin, e.g., such as a LRP6 modulatory agent. Also provided are active agents suitable for use in the subject methods, as well as pharmaceutical preparations thereof.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the subject invention, a more detailed review of embodiments of the methods is first provided, followed by a review of embodiments of utilities in which the methods find use and embodiments of compositions that find use in the methods.

Methods

Aspects of the invention include methods of modulating entry of anthrax toxin into a cell. By modulating is meant either enhancing or inhibiting entry of an anthrax toxin into a cell, where in certain embodiments the methods are methods of inhibiting entry of an anthrax toxin into a cell. By enhancing anthrax toxin entry into a cell is meant that the amount of anthrax toxin that enters a cell, measured using any convenient protocol, is increased by 2-fold or more, such as by 5-fold or more and including by 25-, 50-, 100-fold or more, as compared to a control, i.e., a cell that is not subjected to the methods of the present invention. Likewise, by inhibiting anthrax toxin entry into a cell is meant that the amount of anthrax toxin that enters a cell, as measured using any convenient protocol, is decreased by an amount of 2-fold or more, usually by 5-fold or more and including by 25-, 50-, 100-fold or more, as compared to a control, i.e., a cell that is not subjected to the methods of the present invention. In certain embodiments, the methods are methods of inhibiting entry of anthrax toxin into a cell, such that the cell does not die upon exposure of the cell to anthrax toxin.

The anthrax toxin whose entry into a cell is modulated, e.g., inhibited, via the subject methods is one that is produced by *B. anthracis*. In certain embodiments, the anthrax toxin of interest is one or more of protective antigen (PA), lethal factor (LF) and edema factor (EF). In certain embodiments, the methods result in a decreased presence, e.g., of free cytosolic LF and/or EF in the cell cytosol following exposure of the cell to *B. anthracis*, as compared to a control (e.g. by an amount of 2-fold or more, usually by 5-fold or more and including by 25-, 50-, 100-fold or more).

Aspects of the invention include contacting a cell with an effective amount an agent that modulates, such as inhibits, toxin entry into the cell. In certain embodiments, the agent is one that inhibits entry of the toxin into the cell. In certain embodiments, the agent is one that inhibits toxin entry mediated by a cell surface protein, such as a protein of the cell having an extracellular domain. In certain embodiments, the agent is an agent that modulates, e.g., inhibits, LRP6 toxin mediated cellular entrance or internalization.

As such, in certain embodiments, the agent is an LRP6 modulatory agent. By "LRP6" modulatory agent is meant an agent that in some way changes or alters anthrax toxin entry into the cell that is mediated by LRP6. In other words, the agent enhances or inhibits LRP6 mediated entry of anthrax toxin into the cell, where modulation is determined in reference to an appropriate control.

Low density lipoprotein-related receptor protein 6 (LRP6) is a member of a gene family encoding low-density lipoprotein receptors (LDLR) that reside on the cell surface and participate in endocytosis of their ligands. As a component of a cell surface complex that includes the Wnt and the Wnt-associated protein Frizzled (Fz), LRP6 has also been shown to participate in the transduction of morphogenic signals from Wnt to the growth-regulating protein β-catenin. The mRNA sequence for human LRP6 has been deposited and assigned Accession No. NM_002336 and the protein has been assigned Accession No. NP_002327.

The modulatory agent that is employed in the subject methods may be any agent that, upon contact with the cell, changes the LRP6 mediated entry of anthrax toxin into the cell.

In certain embodiments, the agent is an agent that modulates, e.g., inhibits, binding of PA to LRP6. For inhibiting binding between PA and LRP6, an agent that acts as member of a specific binding pair with LRP6, and thereby inhibits binding of PA to LRP6, may be employed.

The term "specific binding member" or "binding member" as used herein refers to a member of a specific binding complex of molecules, e.g., two or more molecules, where the molecules may be the same or different molecules, where one of the molecules (i.e., first specific binding member) through chemical or physical means specifically binds to the other molecule(s) (e.g., second specific binding member). The complementary specific binding members are sometimes referred to as a ligand and receptor; or receptor and counter-receptor. For the purposes of the present invention, the binding members may be known to associate with each other, for example where an assay is directed at detecting compounds that interfere with the association of a known binding pair. Alternatively, candidate compounds suspected of being a binding partner to a compound of interest may be used. The specific binding pairs may include analogs, derivatives and fragments of the original specific binding member. For example, a receptor and ligand pair may include peptide fragments, chemically synthesized peptidomimetics, labeled protein, derivatized protein, etc:

In certain embodiments, the specific binding member is an antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies that bind specifically to the LRP6 target are referred to as anti-LRP6 target antibodies. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be polyclonal antibodies, although monoclonal antibodies are employed in certain embodiments because they may be reproduced by cell culture or recombinantly, and can be modified to reduce their antigenicity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, an LRP6 antigen comprising an antigenic portion of the LRP6 targets polypeptide, e.g., found on an extracelluar domain, is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the brain tumor protein target, a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

In certain embodiments, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, which may be primed with pristane, or some other tumor-promoter, and immunosuppressed chemically or by irradiation, may be any of various suitable strains. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

In certain embodiments, recombinant antibodies are produced in a recombinant protein production system which correctly glycosylates and processes the immunoglobulin chains, such as insect or mammalian cells. An advantage to using insect cells, which utilize recombinant baculoviruses for the production of antibodies, is that the baculovirus system allows production of mutant antibodies much more rapidly than stably transfected mammalian cell lines. In addition, insect cells have been shown to correctly process and glycosylate eukaryotic proteins, which prokaryotic cells do not. Finally, the baculovirus expression of foreign protein has been shown to constitute as much as 50-75% of the total cellular protein late in viral infection, making this system an excellent means of producing milligram quantities of the recombinant antibodies.

Antibodies with a reduced propensity to induce a violent or detrimental immune response in humans (such as anaphylactic shock), and which also exhibit a reduced propensity for priming an immune response which would prevent repeated dosage with the antibody therapeutic or imaging agent are preferred for use in the invention. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals that have been genetically altered to produce human immunoglobulins. Techniques for generating such animals, and deriving antibodies therefrom, are described in U.S. Pat. Nos. 6,162,963 and 6,150,584, incorporated fully herein by reference.

Alternatively, single chain antibodies (Fv, as described below) can be produced from phage libraries containing human variable regions. See U.S. Pat. No. 6,174,708. In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., polyglycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879-5883 (1988) and Bird et al., Science 242:423-426 (1988), both fully incorporated herein, by reference.

In addition, derivatized immunoglobulins with added chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention. For convenience, the term "antibody" or "antibody moiety" will be used throughout to generally refer to molecules which specifically bind to an epitope of the LPR6 protein targets, although the term will encompass all immunoglobulins, derivatives, fragments, recombinant or engineered immunoglobulins, and modified immunoglobulins, as described above.

Candidate antibodies can be tested for activity by any suitable standard means. As a first screen, the antibodies may be tested for binding against the immunogen, or protein. As a second screen, candidates may be tested for binding to an appropriate cell line. For these screens, the candidate antibody may be labeled for detection. After selective binding to the protein target is established, the candidate antibody agent may be tested for appropriate activity (i.e., the ability to confer anthrax toxin resistance on cells) in an in vitro or in vivo model.

Instead of the above-described antibodies and binding mimetics thereof, other agents that disrupt binding of PA to LRP6 and thereby inhibit LRP6 mediated anthrax toxin entry into the cell may be employed. Other agents of interest include, among other types of agents, small molecules that bind to the LRP6 and inhibit its binding to PA. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups for structural interaction with proteins, particularly hydrogen bonding, and may include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In certain embodiments, the agent may be agent that modulates, e.g., inhibits, expression of functional LRP6. Inhibition of LRP6 expression may be accomplished using any convenient means, including use of an agent that inhibits LRP6 expression, such as, but not limited to: antisense agents, RNAi agents, agents that interfere with transcription factor binding to a promoter sequence of the LRP6 gene, etc.), inactivation of the LRP6 gene, e.g., through recombinant techniques, etc.

For example, antisense molecules can be used to downregulate expression of LRP6 in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted repressor protein, and inhibits expression of the targeted repressor protein. Antisense molecules inhibit gene expression through various mechanisms, e.g., by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides may be 7 or more, such as 12 or more, including 20 or more nucleotides in length, and in certain embodiments are 500 or less, such as 50 or less, including 35 or less nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

In addition, the transcription level of a LRP6 can be regulated by gene silencing using RNAi agents, e.g., double-strand RNA (Sharp (1999) *Genes and Development* 13: 139-141). RNAi, such as that which employs double-stranded RNA interference (dsRNAi) or small interfering RNA (siRNA), has been extensively documented in the nematode C. elegans (Fire, A., et al, *Nature,* 391, 806-811, 1998) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in WO 03/010180 and WO 01/68836, all of which are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

In another embodiment, the LRP6 gene is inactivated so that it no longer expresses a functional protein. By inactivated is meant that the gene, e.g., coding sequence and/or regulatory elements thereof, is genetically modified so that it no longer expresses functional LRP6 protein, e.g., at least with respect to LRP6 mediated anthrax toxin cell entry. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination include those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

Also of interest in certain embodiments are dominant negative mutants of LRP6, where expression of such mutants in the cell result in a modulation, e.g., decrease, LRP6 mediated anthrax toxin entry into the cell. Dominant negative mutants of LRP6 are mutant proteins that exhibit dominant negative LRP6 activity. As used herein, the term "dominant-negative LRP6 activity" or "dominant negative activity" refers to the inhibition, negation, or diminution of certain particular activities of LRP6, and specifically to LRP6 mediated anthrax toxin entry into a cell. A representative embodiment of such a mutant is reviewed in the experimental section, below. Dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc. A mutant polypeptide may interact with wild-type polypeptides (made from the other allele) and form a nonfunctional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz (1987) Nature 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

Contact of the cell with the LRP6 modulatory agent may occur using any convenient protocol. The protocol may provide for in vitro or in vivo contact of the modulatory agent with the target cell, depending on the location of the target cell. Contact may or may not include entry of the agent into the cell. For example, where the target cell is an isolated cell and the modulatory agent is an agent that modulates expression of LRP6, the modulatory agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the modulatory agent, and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the modulatory agent may be administered to the organism or subject in a manner such that the agent is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body.

In the subject methods, the active agent(s) may be administered to the targeted cells using any convenient means capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal; intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et a. (1992), *Anal Biochem* 205:365-368. The DNA may be coated onto gold microparticles, and delivered intradermally by a particle bombardment device, or "gene gun" as described in the literature (see, for example, Tang et a. (1992), *Nature* 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

As reviewed above, the subject methods result in modulation of anthrax toxin entry into a target cell or cells, where the target cell(s) may be in vitro or in vivo. In certain embodiments, the subject methods result in inhibition of anthrax toxin entry into a target cell(s). In certain embodiments, the methods result in a reduction of anthrax toxin susceptibility of cell, e.g., as measured using the assay protocols described in the experimental section below.

While the above description of the subject invention is focused on cellular entry of anthrax toxin by LRP6 binding and internalization, this description is not meant to be limiting. As such, embodiments of the subject invention include those in which the above described modulatory agents target different cell surface receptors and/or different toxins. For example, certain embodiments of the invention are drawn to modulating agents for LRP6 that modulate the entry of a toxin other than anthrax toxin into a cell. As such, aspects of the invention include embodiments of modulating LRP6 mediated entry of a toxin into a cell. Certain other embodiments of the invention include modulatory agents for low-density lipoprotien family members other than LRP6 (for review of low-density lipoprotein family, see Front Biosci. 2001 6:D417-28, incorporated herein by reference). In these embodiments, these modulatory agents function to modulate the entry of an active toxin into a cell. As such, embodiments of the invention include modulating LRP mediated entry of an active toxin into a cell (e.g., as opposed to a protoxin, such as a toxin in an unactive form).

The above methods find use in a variety of different applications. Certain applications are now reviewed in the following Utility section.

Utility

The methods find use in a variety of therapeutic applications in which it is desired to decrease anthrax toxin entry into a target cell or collection of cells, where the collection of cells may be a whole animal or portion thereof, e.g., tissue, organ, etc. In such methods, an effective amount of an LRP6 modulatory agent is administered to the target cell or cells, e.g., by contacting the cells with the agent, by administering the agent to the animal, etc. By effective amount is meant a dosage sufficient to modulate LRP6 mediated anthrax toxin entry into the cell, as desired.

The subject methods find use in the treatment of a variety of different conditions in which the modulation, e.g., enhancement or decrease, of LRP6 mediated anthrax toxin cell entry is desired. In representative embodiments, the methods are employed to modulate an anthrax toxin mediated condition in a subject. In certain of these embodiments, the methods are methods of prophylactically conferring an anthrax toxin resistant phenotype on the subject, such that the subject can later be exposed to *B. anthracis* and not suffer from subsequent anthrax toxin mediated disease conditions, as reviewed above. In certain embodiments, the methods are employed to treat a subject suffering from an anthrax mediated disease condition resulting from exposure to *B. anthracis*. In certain of these embodiments, the methods include first diagnosing the presence of such a condition in the subject. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition. In certain of the embodiments, the subject methods find use in the treatment of host having a "late-stage" disease condition, where a substantial amount of anthrax toxin is present in the host and the condition is no longer treatable by targeting the pathogen itself.

As indicated above, LRP6 is a co-receptor for members of the Wnt family of proteins. Interfering with the interaction of LRP6 and Wnt, e.g., by the binding of the Wnt-signaling inhibitor protein Dkk-1 to LRP6, antagonizes Wnt-mediated signaling in cells (Nusse et al., 2001 *Nature*, 411:255-256). As such, the LRP6 modulatory agents of the present invention find use in modulating Wnt-mediated signaling activity in a cell.

In certain embodiments, LRP6 modulating agents of the invention are used in methods to treat a subject having a condition associated with aberrant Wnt signaling, including, but not limited to, neoplastic diseases, e.g., cancer, Alzheimer's disease, kidney disorders, cardiac and vascular disease, inflammatory disorders, schizophrenia, osteoporosis, and mood disorders. The subject methods are useful for both prophylactic and therapeutic purposes. Thus, as used herein, the term "treating" is used to refer to both prevention of disease and treatment of a pre-existing condition.

In certain embodiments, the LRP6 modulatory agent is an inhibitory agent and the condition being treated is associated with increased or unregulated Wnt signaling. For example, the LRP6 modulatory agent can be an antibody specific for LRP6 which blocks the interaction of LRP6 with Wnt (e.g., similar to the way in which Dkk1 inhibits Wnt signaling), such as the LRP6 specific antibodies described in the experimental section below. In these embodiments, the inhibitor composition is administered to a patient suffering from a condition characterized by aberrant Wnt signaling (e.g., cancer) in an amount sufficient to cure or at least partially arrest the disease and its complications. An amount adequate to accomplish this is defined as a "therapeutically effective dose." Amounts effective for this use will depend upon the severity of the condition/disease and the general state of the subject's health. Single or multiple administrations of the compositions may be administered depending on the dosage and frequency as required and tolerated by the patient. In any event, the composition should provide a sufficient quantity of a LRP6 inhibitory agent of this invention to effectively treat the subject. The particular dose required will depend upon the medical condition and history of the patient, the particular condition being treated, as well as other factors such as age, weight, gender, administration route, efficiency, etc.

A "subject" or "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

In certain embodiments, the LRP6 modulatory agents can be used in combination with other therapeutic agents in the methods of the invention. For example, LRP6 inhibitory agents (and thus inhibitors of Wnt signaling) may be used to target or sensitize a cancer cell to other therapeutic agents, such as 5FU, vinblastine, actinomycin D, cisplatin, methotrexate, and the like. In other embodiments, the methods of the invention can be used with radiation therapy and the like.

In some instances the antibody belongs to a sub-type that activates serum complement when complexed with the transmembrane protein thereby mediating cytotoxicity or antigen-dependent cytotoxicity (ADCC). Thus, cancer can be treated by administering to a patient antibodies directed against LRP6 proteins on the surface of cancer cells. Antibody-labeling may activate a co-toxin, localize a toxin payload, or otherwise provide means to locally ablate cells. In these embodiments, the antibody is conjugated to an effector moiety. The effector moiety can be any number of molecules, including labeling moieties such as radioactive labels or fluorescent labels, or can be a therapeutic moiety, such as a cytotoxic agent.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Screening Assays

Also provided by the subject invention are screening assays designed to find LRP6 modulatory agents of the invention, where such agents may find use in a variety of applications, including as therapeutic agents, as described above. The screening methods may be assays which provide for qualitative/quantitative measurements of LRP6 mediated anthrax toxin cell entry activity in the presence of a particular candidate therapeutic agent. The screening method may be an in vitro or in vivo format. Depending on the particular method, one or more of, usually one of, the components of the screening assay may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. A variety of different candidate agents may be screened by the above methods, including any of the representative agents described above. Using the above screening methods, a variety of different therapeutic agents may be identified. Such agents may be find use in a variety of therapeutic applications, as reviewed above.

Pharmaceutical Preparations

Also provided are pharmaceutical preparations of the subject compounds. The subject compounds can be incorporated into a variety of formulations for administration to a subject. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous cyclodextrin solution further comprise dextrose, e.g., about 5% dextrose.

Dosage levels of the order of from about 0.01 mg to about 140 mg/kg of body weight per day are useful in representative embodiments, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day. Those of skill will readily appreciate that dose levels can vary as a function of the specific compound, the severity of the symptoms and the susceptibility of the subject to side effects.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host.

Kits

Kits with unit doses of the compounds, such as in oral or injectable doses, are provided. For example, kits and systems for practicing the subject methods may include one or more pharmaceutical formulations.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Materials & Methods:

A. Cell Culture, Transfection, and Infection

Cell culture, transfection and infection were carried out using variations of methods reported previously (Lu et al., 2004, Proc. Natl. Acad. Sci. U.S.A. 101:17246-17251). Briefly, M2182, a human prostate cell line, was kindly provided by Dr. Joy Ware (Department of Pathology, Medical College of Virginia Campus) and maintained in RPMI 1640 medium (Invitrogen) using supplements as described previously (Bae et al., 1998, Prostate 34:275-282). The RAW264.7 murine macrophage cell line and murine 293T cells were grown in Dulbecco's modified Eagle's medium containing 10% fetal bovine serum. Plasmid DNA transfection was performed by using the FuGENE 6 transfection reagent (Roche, Inc.) or a calcium phosphate technique (Graham and van der Eb, 1973, Virology 52:456-467; Wigler et al., 1978, Cell 14:725-731). Viral infection was performed using lentiviral-based methods (Lu et al., 2004, Proc. Natl. Acad. Sci. U.S.A. 101:17246-17251). Stable clones from transfection or infection were selected using G418 (350 μg/ml), puromycin (1 μg/ml), hygromycin (300 μg/ml), or blasticidin (10 μg/ml).

B. Construction and Screening of the EST-Library

Construction and screening of cDNA libraries were carried out using variations of methods reported previously (Lu et al., 2004, Proc. Natl. Acad. Sci. U.S.A. 101:17246-17251). Briefly, a gene encoding tetracycline-controlled trans-activator (tTA), a chimeric protein composed of the Tet repressor protein (TetR) fused to the VP16 activation domain (AD) of the herpes simplex virus was introduced into the M2182 cells, resulting in the M2182tTA line. A detailed description of the pLEST-based library (i.e., pLEST-LIB) construction was reported in by Lu et al. (2004). pLEST-LIB pools were treated with PA (50 ng/ml) and FP59 (50 ng/ml) for two days, then grown in a toxin-free medium for an extended period until colonies appeared on plates. Treatment with the toxin was repeated once in the same plates to further reduce the background. The PA/FP59 resistant colonies were picked and expanded individually.

C. Plasmid Construction of EST Library and Expression Vectors

Construction and cloning of expression vectors were carried out using variations of methods reported previously (Lu et al., 2004, Proc. Natl. Acad. Sci. U.S.A. 101:17246-17251). Briefly, to make the pATR43 construct, the EST insert of ATR43 was PCR-amplified using ESTF (5'-cacacaggaaa-cagctatg) and ESTR (5'-ttgtaaaacgacggccagtg) primers, and cloned into the pLEST vector 3' of the Tet-regulated lentiviral promoter in antisense orientation relative to the promoter. The expression vector pcDNA3.1 (Invitrogen, Inc.) carrying the CMV promoter was used to make pLRP6 m3 and pLRP6ΔC. pLENTI-SUPER [derived from pSUPER (Brummelkamp et al., 2002, Science 296:550-553)] was used to clone and express both human and mouse lrp6 gene-specific siRNA fragments. To express LRP6 transcripts unaffected by siRNA, silent mutations at 7 sites of the 21-nucleotide sequence targeted by siRNA3 were introduced into LRP6 cDNA resulting in pLRP6 m3. The mutated transcripts were expressed in the pcDNA3.1 vector. To facilitate plasmid construction, an additional silent mutation was created at a site 17 nucleotides upstream of the 21-nucleotide sequence, encoding siRNA (i.e., aggatctcttccaggaatgtctcgaggtaaatcaat was changed to cggatctcttccaggaatgagcagaggaaagtctat. Bold nucleotides represent the segment targeted by siRNA3. Underlined nucleotides indicate the sites of mutational alterations.). The dominant-negative LRP6 variant, LRP6ΔC, was constructed by PCR amplification of a segment of human LRP6 that lacks coding sequences for the cytoplasmic domain of the protein was amplified using human cDNA as template and the following primers: (5'-CGGATCCAAGATGGGGGCCGTC-CTGAGG)(SEQ ID NO:01) and (5'-TAGCGGCCGCTACA-GATCTTCTTCAGAAATAAGTTTTTGTTCCATTCCTG-GAA GAGATCCTG)(SEQ ID NO:02), and subsequently cloned into BamHI and NotI sites of pcDNA3.1. Other DNA constructs for protein expression were kindly provided by Drs. Xi He (LRP6ΔC and pLRP6N-Myc), Stuart Aaronson (Flag-LRP6, Myc-LRP6ΔN), John Young (CMG2-EGFP), Laurie E. Ailles (pcDNA3.1-AxinMyc), Wesley Sundquist (VPS4 and VPS4 (E228Q)). The following constructs were previously described: TEM8-HA (Liu and Leppla, 2003, *J. Biol. Chem.* 278:5227-5234) and TSG101 (M95A) (Bishop and Woodman, 2001, *J Biol Chem* 276:11735-11742; Lu et al., 2003, *Proc. Natl. Acad. Sci. U.S.A.* 100:7626-31).

D. Assay for Luciferase Reporter Gene Activity and EGF Receptor Degradation

These assays were performed as reported in (Veeman et al., 2003, *Curr. Biol.* 13:680-685; Lu et al., 2003, *Proc. Natl. Acad. Sci. U.S.A.* 100:7626-31). Briefly, for each experiment, equal amounts of cells were seeded in 6-well plates about 18 hours prior to transfection to yield confluence of ~70% at the time of transfection. The cells in each well were co-transfected with 0.5 μg of the Super8XTOPflash reporter plasmid (Randall Moon Lab, University of Washington School of Medicine), and 0.05 μg of the pcDNA3.1-lacZ plasmid (Clontech, Inc., Palo Alto, Calif.), using the calcium phosphate precipitation method as per the manufacturer's specifications (Stratagene, La Jolla, Calif.). After 36 hr, the cells were treated with a Wnt induction medium (American Type Culture Collection, Manassas, Va.) for 6 hr prior to lysis in 1× reporter lysis buffer (300 μl/well) (Promega, Madison, Wis.). The lysates were centrifuged at 14,000 RPM for 5 min, and 10 μl of each supernatant was added to 50 μl of luciferase assay substrate (Promega). Luciferase activity was measured at 570 nm using a GENios Multi-Detection Reader (TECAN, Phenix Research Products). Readings were normalized for transfection efficiency by measuring β-galactosidase activity (Coso et al., 1995, *Cell* 81:1137-1146). Assay of EGF receptor degradation was carried out in cells transfected with pcDNA-EGFR (200 ng/well in 6-well plates). Twenty-four hours after transfection, the cells were starved in Opti-MEM medium overnight before being mock-treated or induced with 150 ng/ml EGF for 90 min. Cell lysates were then subjected to immunoblotting using an anti-EGFR polyclonal antibody.

E. Real Time RT-PCR

Total RNA was isolated using the RNeasy kit (Qiagen, Inc., Valencia, Calif.). For quantitation, the region of LRP6 transcripts was amplified using the primers, (5'-GGAGATGC-CAAAACAGACAAG-3')(SEQ ID NO:03) and (5'-C-3') (SEQ ID NO:04). The primers used to amplify a region of the β-actin mRNA were: (5'-GAGGCACTCTTCCAGCCTTC-CTT)(SEQ ID NO:05) and (5'-GCGTACAGGTCTTTGCG-GATGT)(SEQ ID NO:06). β-actin transcript abundance was measured as an internal control. Real-time quantitations were performed using the Bio-Rad iCycler iQ system (Bio-Rad). The fluorescence threshold value was calculated using iCycler iQ system software.

F. Toxin Treatment and Cell Viability Assay

Proteins produced as described previously (Leppla, 1988, *Methods Enzymol.* 165:103-116) include wild type PA, FP59 and LF. Cytotoxicity assays for M2182 were performed by treating cells at a concentration of $5 \times 10^4$ cells/well (in 6-well plates) with PA (30 ng/ml) plus FP59 (50 ng/ml) for two days. Cells were cultured in toxin-free medium for three days after toxin challenge before being stained with crystal violet for microscope imaging and photography. For MTT assay, cells were seeded in 96-well plates (100 μl/well) one day prior to toxin treatment; the cell concentration used was $5 \times 104$/ml for M2182 cell line and $3 \times 10^4$/ml for RAW264.7 cell line. Various concentrations of PA combined with a fixed concentration of FP59 (50 ng/ml) (for M2182 line) or LF (500 ng/ml) (for RAW264.7 line) were added to wells, and cells were incubated for 48 hours at 37° C. Cell viability was measured by adding 3-[4,5-dimethylthiazol-2-yl]-2,5-diphenyltetrazolium bromide (MTT) (Sigma) to a final concentration of 1 mg/ml for 1 hr at 37° C. The supernatant was carefully removed before the addition of 50 μl of solubilization solution (10% SDS in 0.01 N HCl), and subsequently of 200 μl of PBS to each well. Spectrophotometer readings at 570 nm were determined using a GENios Multi-Detection Reader (TECAN, Phenix Research Products). Cell viability was normalized to wells lacking PA. Each data point shown in figures for MTT assays represents the averaging of results from 8 wells.

G. Preparation of LRP6-Specific Short Interfering RNAs (siRNAs)

Three human-specific lrp6 sequences (tgctacgattgtagttgga (SEQ ID NO:9), cgaatcgaattgaggtgtc (SEQ ID NO:10), tgtctcgaggtaaatcaat) (SEQ ID NO:11)and three murine -specific lrp6 sequences (gagaatgcaacgattgtag(SEQ ID NO:12), gtgctttgtttaattgatc(SEQ ID NO:13), atacacatctggttgagat) (SEQ ID NO:14)were selected. The siRNA duplexes were cloned into the pLENTI-SUPER lentiviral vector [derived from pSUPER (Brummelkamp et al., 2002, *Science* 296:550-553)]. siRNA constructs were then introduced into cells by infection. Stable clones of cells carrying siRNAs were selected using blasticidin (10 μg/ml)(Sigma). The scrambled siRNA control was a product from Ambion (Austin, Tex.).

H. Biochemical Assay of PA Binding and Internalization

Methods were as described by Liu et al. (2003 *J. Biol. Chem.* 278:5227-5234; and 2003, *Expert Opin. Biol. Ther.* 3:843-853), except that the final concentration of PA and its incubation time were 0.05 μg/ml for 2 hr, and 1 μg/ml for 45 min, respectively.

I. Western Blotting and Co-Immunoprecipitation

Western blotting was performed essentially as described by Harlow and Lane (1999, *Using Antibodies: A Laboratory Manual*, Cold Spring Harbor Lab. Press, Plainview, N.Y.) using precast 10% or 3-8% gels (Criterion XT Precast Gel, Bio-Rad) for electrophoresis and standard conditions. The soluble cell proteins were quantitated using the BCATM protein assay kit (Pierce Biotechnology, Inc.). For co-immunoprecipitation assays, 293T cells, 48 hr after transfection, were lysed in NP40 buffer containing a protease inhibitor cocktail (Complete Mini, Roche Diagnostics, Inc.). The lysates were centrifuged at 16,000×g, and the soluble fraction was immunoprecipitated with the desired antibody-conjugated agarose beads (Santa Cruz Biotechnology, Inc.). The cell medium was included in LRP6N-Myc immunoprecipitation reactions because LRP6N-Myc is secreted into the supernatant (Tamai et al., 2000, *Nature* 407:530-535) after being expressed.

J. Antibody Reagents

Polyclonal antibody against PA was generated as described in Liu et al.,(2003, *Expert Opin. Biol. Ther.* 3:843-853), and monoclonal antibody against PA was ordered from Novus Biologicals (NB 600-407). Rabbit polyclonal antibody against human LRP6 (H300) was purchased from Santa Cruz Biotechnology, Inc. and monoclonal anti-LRP5/6 antibody generated against a synthetic peptide derived from an amino acid sequence (DTGTDRIEVTR (SEQ ID NO:15))of the second YWTD (SEQ ID NO:16)repeat of LRP6 was obtained from A&G Pharmaceuticals (Baltimore, Md.) and BioVision (Mountain View, Calif.). Rabbit polyclonal antibodies N204 & N251 were generated for us by Proteintech Group, Inc. (Chicago, Ill.) using synthetic peptides derived from amino acid sequences (NFIHKSNLDGTNRQAVVKGS (SEQ ID NO:07) for N204, and C (SEQ ID NO:08) for N251). Agarose-conjugated monoclonal antibodies of c-Myc (9E10), HA (F-7), and GFP (B-2), and horse radish peroxidase (HRP)-conjugated monoclonal antibodies against c-Myc (9E10), HA (F-7) and GFP (B-2) were all obtained from Santa Cruz Biotechnology, Inc. Anti-Flag (M2) monoclonal antibodies against the HRP-conjugate and affinity gels used for co-IP experiments were obtained from Sigma,Inc.

K. Immunofluorescence Microscopy

PA protein was labeled with Alexa Fluor 488 using the protein labeling kit (A-10235, Molecular Probes, Inc.). The potency of PA after labeling was fully retained as indicated by the MTT assay (data not shown). The concentrations of PA-Alexa 488 used in anlysis of PA binding and processing were 0.6 µg/ml and 1 µg/ml, respectively. Immunostaining was performed according to a standard protocol (Harlow and Lane, 1999, *Using Antibodies: A Laboratory Manual*, Cold Spring Harbor Lab. Press, Plainview, N.Y.). The primary antibody anti-Flag (M2) (murine monoclonal, Sigma, Inc.) was used at a dilution of 1:200. Alexa-Fluor 594 goat anti-mouse IgG (Molecular Probes) was used as the secondary antibody at a dilution of 1:400. The pre-conjugated antibody anti-HA-Alexa Fluor-594 (murine monoclonal IgG1, 16B12, Molecular Probes) was also used. The cover slips were mounted onto slides with a ProLong® Gold antifade reagent containing DAPI solution (Molecular Probes), and cells were examined under a deconvolution microscope (Applied Precision, Issaquah, Wash.).

L. Antibody Protection Assay $3 \times 10^4$/ml of RAW264.7 cells were first seeded in 96-well plates (100 µl/well) the day prior to the assay. The cells were then incubated at 37° C. for 48 hr with 3 ng/ml of PA, 500 ng/ml of LF and serial dilutions of antibodies. To test the specificity, the antibody was pre-absorbed with the N204 or the N251 peptide prior to assay. The antibody was incubated with peptide in the ratio of 2 mg peptide/1 ml final bleed on a rotator at 4° C. over night, followed by a centrifugation at 14,000 RPM for 10 min to remove the precipitate. Toxin sensitivity was determined by the cell viability as described above.

II. Results

A. Isolation and Characterization of Cells Showing Decreased Toxin Susceptibility A phenotypic screen was designed to discover cellular genes that specifically affect the actions of PA in the pathway to anthrax toxicity. In these experiments, we used a transactivated tetracycline (Tet)-controlled promoter [Tet-off system, (Gossen and Bujard, 1992, Proc. Natl. Acad. Sci. U.S.A. 89:5547-5551; Gossen et al., 1995, Science 268:1766-1769)] on the lentiviral vector pLEST to activate antisense transcription ~40,000 human ESTs (Lu et al., 2004, *Proc. Natl. Acad. Sci. U.S.A.* 101:17246-17251) introduced into a population of M2182 human prostate carcinoma cells. We then isolated clones resistant to killing by a mixture of PA and FP59, a fusion of the PA-binding domain of LF to the ADP ribosylation domain of *Pseudomonas aeruginosa* exotoxin A. As PA enables the entry of FP59 into cells and exotoxin-A mediated lethality (Arora and Leppla, 1993, *J Biol Chem.* 268:3334-41), we reasoned that cells made defective in PA internalization by antisense expression of ESTs would show decreased killing by PA+FP59.

Screening of a cell library having an estimated complexity of $2 \times 10^5$ independent insertions of the pLEST construct in chromosomes of M2182 cells yielded 73 colonies resistant to PA+FR59, nine of which showed down-regulation of resistance by tetracycline. ATR43, a clone that survived a PA concentration >25-fold the concentration that was lethal in the parental cell line when combined with 50 ng/ml of FP59) (FIG. 1A) was selected for further study. Growth of ATR43 cells for 48 hours in the presence of Tet (1 µg/ml), decreased their ability to survive exposure to the toxin while having little effect on growth of the parental line (FIG. 1B).

Analysis of the PCR-amplified EST present in ATR43 revealed a single chromosomally-integrated sequence that corresponds to a ~228 nt image clone [image clone 285207, accession number N66273 (Hillier et al., 1996, *Genome Res.* 6:807-828)] annotated in Genbank as an intron located between exons 21 and 22 of the low-density lipoprotein receptor-related protein 6 (lrp6) gene. This cDNA had been cloned in pLEST 3' to the Tet-regulated lentiviral promoter and in antisense orientation relative to the promoter.

B. Decreased Expression of LRP6 Results in Toxin Resistance

Western blot analysis of ATR43 cell extracts (FIG. 1C) indicated decreased intensity of bands migrating at the previously identified positions of LRP6 monomer and dimer (Liu et al., 2003, *Mol. Cell. Biol.* 23:5825-5835), as detected with murine monoclonal antibody directed against an epitope present in both LRP6 and the related protein, LRP5. We confirmed the identity of these bands as LRP6 monomers and dimers by electrophoresis of lysates containing a N-terminally-tagged Flag-LRP6 protein in SDS-PAGE in the presence of the reducing agent β-mercaptoethanol (β-ME), followed by immunoblotting with anti-Flag antibody (FIG. 1D); the two highly reproducible faint bands migrating more slowly than the Flag-tagged LRP6 dimer (FIG. 1C) may represent multimeric forms of LRP6. The biological effects of reduction of LRP6 protein in ATR43 were evident also from the observed impairment of the cellular response of this clone to Wnt, as indicated by sharply decreased activity of a β-catenin regulated promoter on the Super8XTOPflash reporter plasmid (Veeman et al., 2003, *Curr. Biol.* 13:680-685), which was introduced into this cell clone (FIG. 1E).

While the above experiments argue strongly for the role of LRP6 in the phenotype observed for ATR43 cells, assignment of the EST sequence that mediates tetracycline-dependent regulation of toxin resistance in ATR43 cells to a region of the lrp6 gene that has been annotated in Genbank as an intron, prompted additional studies to further establish the causal role of LRP6 deficiency in toxin resistance. Firstly, a plasmid (pATR43) containing cDNA of image clone 285207 was newly inserted into the pLEST vector in antisense orientation with respect to the Tet-regulated promoter, was introduced into naïve M2182tTA cells. As was observed for ATR43, these cells showed decreased sensitivity to PA+FP59 (FIG. 1F), confirming the role of the EST sequence in toxin resistance. The effects of inactivating Lrp6 on the sensitivity of M2182 cells to PA+FP59 was further confirmed in cell clones that stably produced 21-23 nt siRNAs complementary to three different exonic sequences of Lrp6 mRNA. Down-regulation of Lrp6 transcripts by two of these siRNAs, siRNA1 and siRNA3, was observed by quantitative RT-PCR (FIG. 1G), along with 1) reduction of the steady state level of LRP6 protein as indicated by the summed densities of LRP6 monomer and multimer bands (FIGS. 1H and I), 2) an impaired cellular response to Wnt activation (FIG. 1E), and 3) reduced toxin susceptibility (FIG. 1J); pre-absorption of the peptide employed as immunogen resulted in disappearance of the Western blot signals (FIG. 1I, middle panel), although the ratio of LRP6 monomer and dimer varied in different experiments and for different LRP6 antibodies.

That the observed siRNA effects on toxin-induced lethality resulted from inhibition of LRP6 function was further confirmed by concurrent overexpression of full-length Lrp6 cDNA in two independent toxin-resistant clones (FIG. 1K; M2182/siRNA3 carrying pLRP6 m3-4 or pLRP6 m3-8 vs. M2182/siRNA3 carrying pcDNA3.1 vector alone). In these experiments, we created silent mutations at 7 sites in the 21-nucleotide sequence targeted by the siRNA to prevent siRNA3 inhibition of the overexpressed Lrp6 cDNA. Using a fixed concentration of FP59 (50 ng/ml), the calculated values of EC50 (effective concentration of PA required to kill 50% of cells tested) were increased 4.3- to 5.1-fold (calculated values for M2182, M2182/siRNA3_pLRP6 m3-4, M2182/siRNA3_pLRP6 m3-8, and M2182/siRNA3_pcDNA3.1 are $3\times10^{-11}$ M, $5.4\times10^{-10}$ M, $4.5\times10^{-10}$ M, and $2.3\times10^{-9}$ M, respectively).

C. LRP6 Deficiency Results in Impaired Binding and Internalization of PA

The known cell surface location and previously elucidated biological roles of LRP6 suggested that of LRP6 deficiency might alter toxin lethality by impairing PA functions. To test this hypothesis, we examined the effects of Lrp6-specific siRNAs on the ability of native anthrax toxin (i.e. PA+LF) to kill macrophages, which are a natural target for LF. Three siRNAs corresponding to sequences of the murine lrp6 gene were inserted in the pLENTI-SUPER vector and expressed stably in the murine macrophage cell line RAW264.7. Controls were non-transfected RAW264.7 cells and cells expressing siRNA1 directed against a human lrp6 sequence absent in the mouse gene. As shown in FIG. 2A, MTT assay demonstrated increased survival in each of the three mouse-sequence-specific lrp6 siRNA pools of clones exposed to PA+LF.

Western blot analysis of lysates from M2182 cells made resistant to toxin by either siRNA or antisense RNA against LRP6 transcripts showed a decrease in 83 kDa PA monomer bound to the cell surface (FIG. 2B) and reduction of an SDS-resistant oligomeric form of PA that characteristically survives proteolytic treatment when cell cultures exposed to toxin complexes at 4° C. are shifted to 37° C. and the toxin complexes are internalized (Liu et al., 2003, *Proc. Natl. Acad. Sci. U.S.A.* 100:7626-31) (FIG. 2C). Additionally, deconvolution fluorescence microscopy using Alexa 488-labelled PA showed that the abundance of PA both at the cell surface (FIG. 2D) and in the cytoplasm (FIG. 2E) was reduced in all LRP6 deficient clones examined, consistent with our biochemical evidence of decreased PA binding and internalization. Internalized PA co-localized with the early endosomal marker EEA1 (data not shown), in agreement with evidence that surface-bound PA complexes are translocated into early endosomes after internalization (Leppla, 1995, *In Handbook of Natural Toxins*, B. I. J. Moss, M. Vaughan, and A. Tu, eds. (New York, Marcel Dekker, Inc.), pp. 543-572).

D. The Intracellular Domain of LRP6 is Essential for PA-Mediated Internalization and Toxin Lethality The data presented above demonstrates that deficiency of LRP6 decreases both binding and internalization of PA. An LRP6 mutant protein (i.e., LRP6ΔC) that lacks most of the cytoplasmic domain (FIG. 2F) and has been reported to have dominant negative effects on Wnt signaling mediated by the co-existing wild type LRP6 protein (Tamai et al., 2000, *Nature* 407:530-535) and an additional truncated LRP6 mutant protein that we expressed from pcDNA3.1 were tested for their ability to block PA-mediated cytotoxicity of FR59 in M2182 cells. Cell populations expressing each LRP6ΔC mutant proteins were treated with PA (50 ng/ml)+FP59 (50 ng/ml) for two days, followed by extended growth on toxin-free medium. Whereas no survivors were observed among naïve M2182 cells or cells transfected with pcDNA3.1, colonies were seen within several days in cells expressing the pLRP6ΔC proteins (data not shown). Randomly picked clones from transfected cells containing the LRP6ΔC expression constructs were expanded to generate the M2182/pLRP6ΔC-1 and M2182/pLRP6ΔC-8 cell lines; assay of β-catenin in these lines showed sharply reduced Wnt signaling (FIG. 2G), confirming the dominant-negative effects of the LRP6ΔC proteins. Both clonal lines showed a dramatic and highly reproducible decrease in killing by PA+FP59 (FIG. 2H). Moreover, whereas binding of the 83 kDa PA monomer to the cell surface was not detectably affected by overexpression of LRP6ΔC mutant proteins (FIG. 21), PA internalization, as monitored by the presence of PA oligomer after shift of the cell culture to 37° C., was impaired (FIG. 2J). These results show that LRP6 plays an essential role in accomplishing the internalization of PA and consequently in conferring cellular susceptibility to anthrax toxin. Moreover, the observed dominant negative effects of the LRP6ΔC on PA-mediated cell death imply that the intracellular domain of LRP6, unlike the intracellular domain of the PA receptor, ATR/TEM8 (Liu and Leppla, 2003, *J. Biol. Chem.* 278:5227-5234), is essential for toxin lethality.

E. Disruption of Wnt Signaling or of Generalized Mechanisms of Endocytic Trafficking does not Impair Toxin Lethality To address whether disruption of Wnt signaling is the mechanism underlying the resistance of LRP6-deficient cells to PA-mediated toxin lethality, we examined the effects of Axin, which regulates Wnt signaling downstream of entry of the Wnt/receptor complex into cells (Itoh et al., 1998, *Curr. Biol.* 8:591-594, Willert et al., 1999, *Development* 126:4165-4173; Zeng et al., 1997, *Cell* 90:181-192), on the resistance of M2182 cells to PA+FP59. Whereas adventitious expression of Axin prevented induction of β-catenin following addition of Wnt protein to cell cultures (FIG. 3A), susceptibility to PA/FP59 toxin was unaltered by Axin expression (FIG. 3B), indicating that interference with Wnt signaling per se does not result in toxin resistance.

Whether mitigation of anthrax toxin lethality by LRP6 deficiency is associated with more generalized effects on endocytic trafficking was addressed firstly by determining if LRP6-deficient cells show normal internalization and endocytic trafficking of a prototypical cell surface receptor, the epidermal growth factor receptor (EGFR), and secondly by investigating whether cells having broad defects in endocytic trafficking exhibit resistance to toxin lethality. We observed that epidermal growth factor-induced internalization and degradation of EGFR was similar in parental M2182 cells, in clone ATR43, and in cells made toxin resistant by siRNA directed against LRP6 (FIG. 3C). Conversely, cells that overexpress the mutant TSG101 or VPS4 proteins and consequently are broadly defective in endocytic trafficking (Bishop and Woodman, 2001, *J Biol Chem* 276:11735-11742; Lu et al., 2003, *Proc. Natl. Acad. Sci. U.S.A.* 100:7626-31; Strack et al., 2003, *Cell* 114:689-699), showed the expected abnormality of EGFR internalization/degradation (FIG. 3D), but unchanged lethality to PA+FP59 (FIG. 3E). Thus, LRP6 deficiency does not result in a generalized defect in endocytic trafficking and defective endocytic trafficking per se is not sufficient to mitigate toxin effects.

F. LRP6 Protein Interaction with PA Receptors TEM8 and CMG2 is Required for Toxin Internalization Multiple co-immunoprecipitation (co-IP) experiments showed interaction between LRP6 and both of the previously identified cellular receptors for PA (i.e., TEM8 and CMG2) but no direct association of LRP6 with PA (FIG. 4A). In these experiments, the C-terminal Myc-tagged extracellular domain of LRP6 (LRP6N-Myc) was harvested from 293T cell growth medium, and incubated with PA or with lysates containing HA-tagged TEM8 (TEM8-HA) or enhanced green fluorescent protein-tagged (EGFP-tagged) CMG2 (CMG2-EGFP); 293T lysates expressing N-terminal Flag-tagged full-length LRP6 (Flag-LRP6) were also examined by co-IP assay. LRP6 was detected in precipitates of TEM8-HA (FIG. 4B, top), and TEM8 was observed in precipitates of Flag-LRP6 (FIG. 4B, bottom). Similar co-IP experiments carried out using TEM8-HA and LRP6N-Myc, which contains only the extracellular domain of LRP6 (i.e., LRP6N), indicated that this domain is sufficient for interaction with TEM8 (FIG. 4C). In additional experiments, we observed LRP6N in precipitates of CMG2-EGFP (FIG. 4D, top) and found CMG2 in precipitates containing LRP6N-Myc (FIG. 4D, bottom). However, we observed no interaction between either TEM8 or CMG2 and an LRP6 truncated protein lacking the extracellular domain (FIG. 4E). As the precipitated bands from co-IP experiments that detected the interaction of LRP6 and PA receptors were faint in comparison with bands in the positive control lanes (FIGS. 4B-4D), we suspect that efficient interaction between LRP6 and PA receptors may involve accessory protein(s) that were not overexpressed in these experiments, and which thus may be present in limiting amounts. Interestingly, while interaction binding of the LRP6 extracellular domain to TEM8 did not require PA, PA expression enhanced this interaction (FIG. 4F); we have not observed enhancement of the LRP6—CMG2 interaction by PA (data not shown).

As LRP6 initiates Wnt signaling when it enters cells together with other members of a Wnt-based complex (Mao et al., 2001, *Nature* 411:321-325), we hypothesized that LRP6 may function similarly to promote internalization of PA and its receptors; deconvolution fluorescence microscopy experiments provided evidence of just such a role. As has been observed previously (Cong et al., 2004, *Development* 131:5103-5115), in the absence of PA deconvolution microscopy showed that Alexa Fluor-594-stained (red) Flag-labelled LRP6 was present mainly in the cytoplasm as well as on the cell surface (FIG. 5A). Addition of PA altered the location of internalized red fluorescent LRP6, resulting in its polar aggregation within the cytoplasm (FIG. 5B). Furthermore, green fluorescence-labeled PA co-localized with cytoplasmic LRP6 (FIG. 5B), and also with internalized TEM8 (FIG. 5C). We were not able routinely to overexpress LRP6 concurrently with either TEM8 or CMG2 in the same cells (M2182); however, in rare instances where concurrent overexpression of both Flag-LRP6 and CMG2-EGFP was achieved, co-localization of LRP6 and CMG2 was observed in cells treated with PA (e.g., FIG. 5D). Expression of siRNA directed against LRP6 or dominant-negative LRP6ΔC prevented the occurrence of cytoplasmic aggregates of Alexa Fluor-594-stained TEM8-HA (FIG. 5E) and EGFP-labelled CMG2 (FIG. 5F), which normally were observed after incubation of cells with PA for 45 min at 37° C. (FIG. 5E, top panels)—providing further evidence that the PA-mediated internalization TEM8 and CMG2 is dependent on LRP6. Collectively, our immunoprecipitation and fluorescence microscopy results argue strongly that LRP6 forms a complex with PA receptors that accomplishes the translocation of PA and the bound toxin moieties into the cytoplasm.

G. LRP6 Antibodies Protect Cells from Anthrax Cytotoxicity

Figure 6:
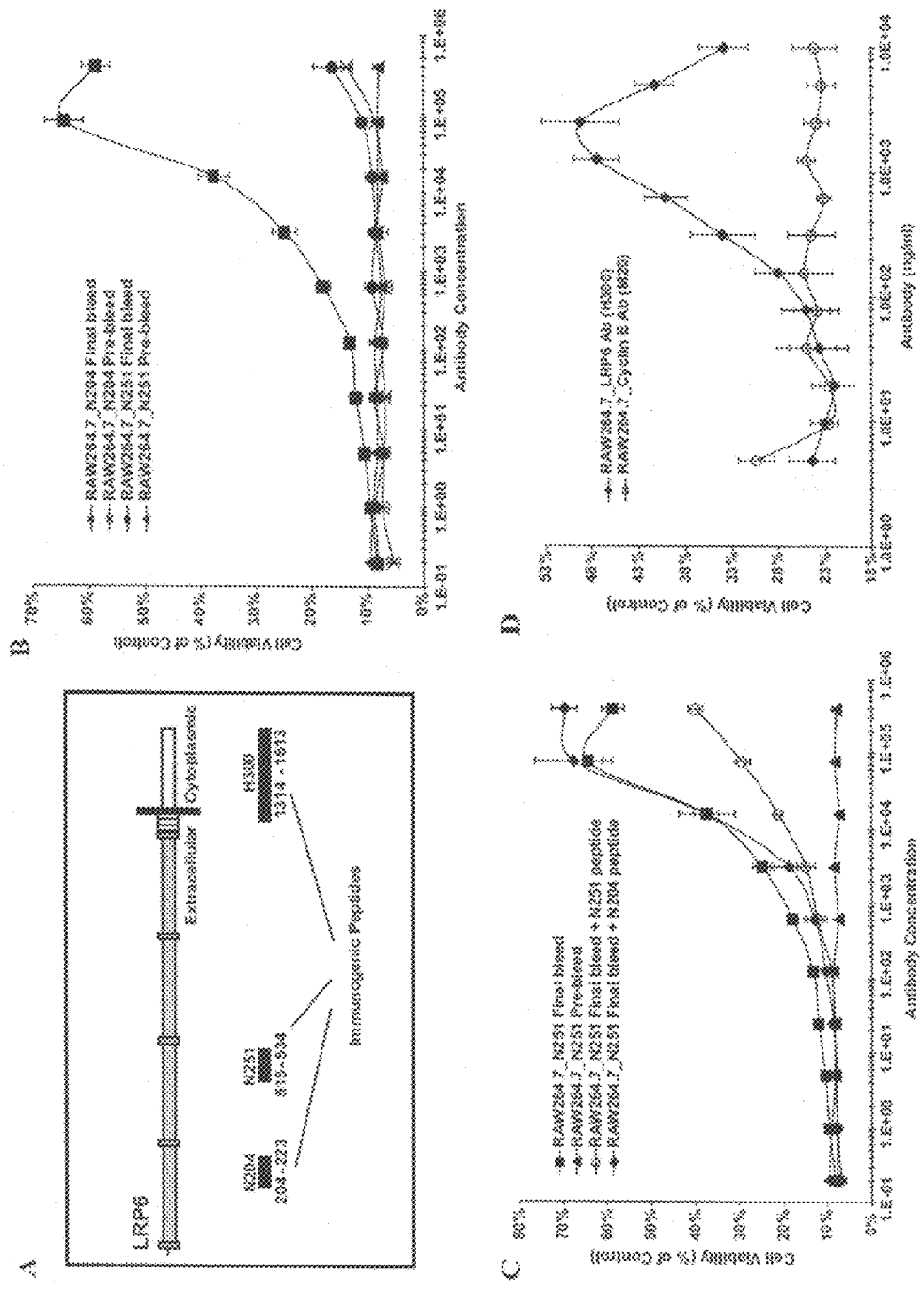
FIGS. 6A to 6D: Effect of LRP6 Antibodies on Cytotoxicity of PA Plus LF. (A) Peptides used as immunogens to produce the antibodies. H300 is a rabbit polyclonal antibody raised against C-terminal of human LRP6 (1314-1613). N251 and N204 are rabbit polyclonal antibodies raised against small peptides targeting different segments of LRP6 extracellular domain. (B-C) Effects of LRP6 N251 and N204 on killing of RAW264.7 cell by PA/LF. Cell viability and the specificity of antibody protection (C) were assessed as described in Experimental Procedures. The antibody concentration is the relative concentration of bleed (1=4.88E+7× dilution). (D) Effect of LRP6 commercially available antibody H300 and rabbit polyclonal antibody raised against Cyclin E (M-20) (both from Santa Cruz Biotechnology, Inc) as a control. The methods used are the same as above (FIG. 6B).

We generated rabbit polyclonal antibodies against two synthetic peptides that correspond to different segments of the extracellular domain of LRP6 and tested these antibodies (N204, directed against amino acids 204-223, and N251, directed against amino acids 515-534; FIG. 6A) for their ability to protect RAW264.7 macrophages from the lethal effects of anthrax toxin (PA+LF). Dosage-dependent increased survival was observed for cells treated with N251, whereas antibody N204 provided no detectable protection from toxin killing (FIG. 6B). Protection by antibody to N251 was partially reversed by the addition of peptide N251, but not by N204 (FIG. 6C). H300, a commercially available rabbit polyclonal antibody generated against a LRP6 human protein fragment (amino acids 1314-1613) that includes a sequence of the cytoplasmic domain as well as segments of the extracellular and transmembrane domains (FIG. 6A), also provided dosage dependent protection against killing by PA+LF (FIG. 6D).

III. Discussion

Using antisense RNA generated intracellularly against a library of ESTs to inactivate chromosomal genes globally in populations of human cells, plus an experimental strategy that selected cell clones resistant to the actions of cytotoxins, we identified genes whose functional inactivation is causally related to toxin resistance. This approach uncovered Irp6, a member of a gene family encoding low-density lipoprotein (LDL) receptor-related proteins (LRPs) that reside on the cell surface and participate in the delivery of a variety of ligands into the cytoplasm (Howard et al., 1996, *J. Clin. Invest.* 97:1193-1203; Kounnas et al., 1995, *Cell* 82:331-340; Li et al., 2001, *J. Biol. Chem.* 276:18000-18006; Orth et al., 1992, *Proc. Natl. Acad. Sci. U.S.A.* 89:7422-7426; Stefansson et al., 1995, *J. Biol. Chem.* 270:19417-19421). The results reported here show that the LRP6 protein, which previously has been known principally as a mediator of the Wnt signaling pathway, has a hitherto unsuspected role in the delivery of anthrax toxins into cells.

Figure 4:
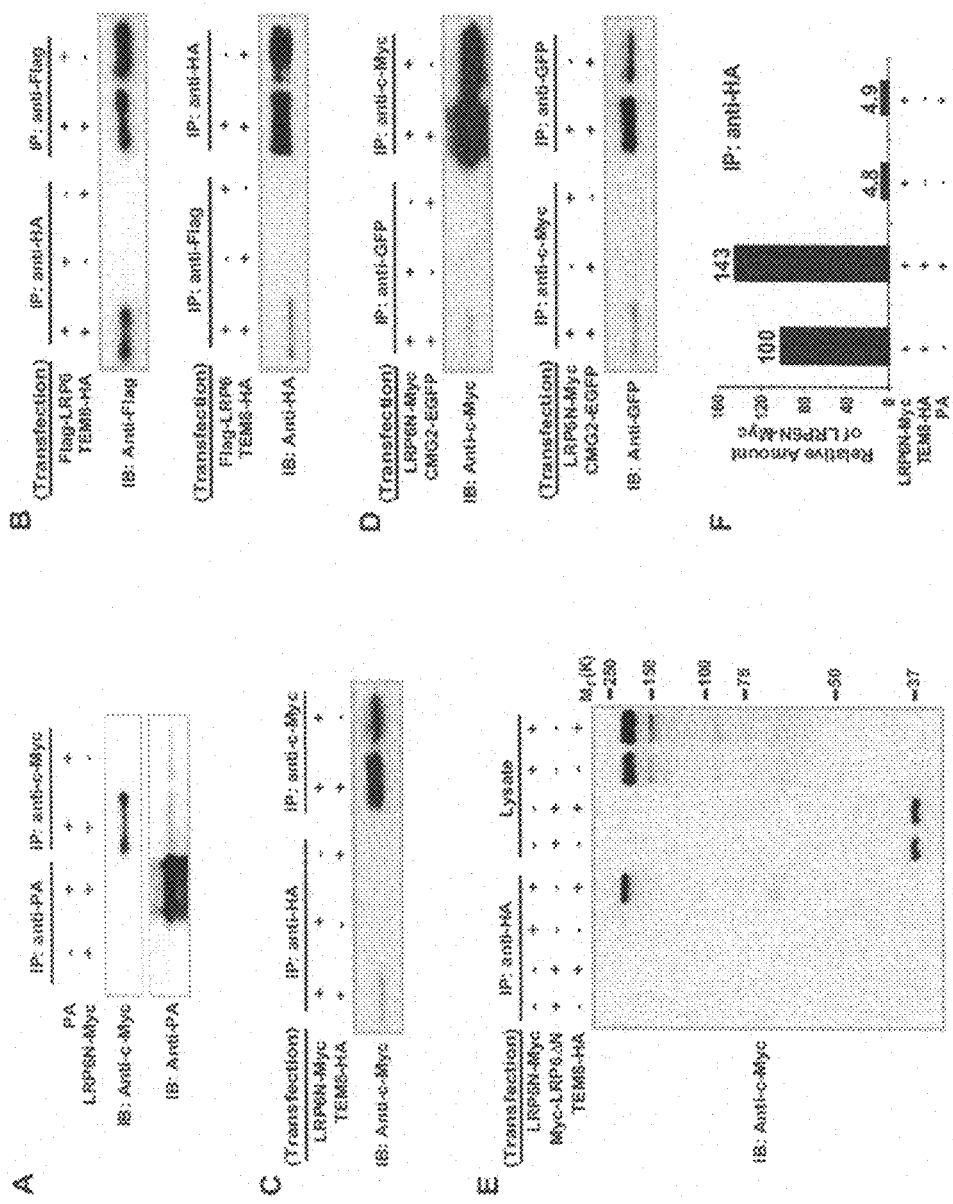
FIGS. 4A to 4F: Binding of LRP6 Extracellular Domain to TEM8 and CMG2. (A) 293T cells were transfected with LRP6N-Myc. Cell medium containing LRP6N-Myc protein was incubated with PA83 on ice for 30 min before being mixed with agarose-conjugated anti-c-Myc antibody or G protein agarose conjugated with PA rabbit polyclonal antibody. After incubation for an additional 3 hours on a rotator in a cold room, the agarose beads were washed and subjected to immunoblot analysis. (B) 293T cells were transfected with Flag-LRP6, TEM8-HA, or both. Cell lysates were treated by addition of anti-HA-conjugated agarose beads or anti-Flag-conjugated affinity gel. The precipitated proteins were then subjected to immunoblot analysis probed with anti-Flag antibody conjugated with horseradish peroxidase (HRP) (top) or anti-HA-HRP (bottom). (C) 293T cells were transfected with LRP6N-Myc, TEM8-HA, or both. Cell lysates plus medium were treated by addition of anti-HA-conjugated or anti-c-Myc conjugated agarose beads. The precipitated proteins were then subjected to immunoblot analysis probed with anti-c-Myc-HRP. (D) 293T cells were transfected with LRP6N-Myc, CMG2-EGFP, or both. Cell lysates plus medium were treated with either anti-GFP-conjugated agarose beads or anti-c-Myc-conjugated agarose beads. The precipitated proteins were then subjected to immunoblot analysis probed with anti-c-Myc-HRP (top), or anti-GFP-HRP (bottom). (E) 293T cells were transfected with LRP6N-Myc, Myc-LRP6ΔN, TEM8-HA, or a combination of two of them. Cell lysates combined with medium were treated with anti-HA-conjugated agarose beads before being subjected to immunoblot analysis probed with anti-c-Myc-HRP. (F) 293T cells were transfected with LRP6N-Myc, TEM8-HA or both. Cell lysates combined with medium were treated with anti-HA-conjugated agarose beads in the presence or absence of PA (0.5 μg/ml) before being subjected to immunoblot analysis probed with anti-c-Myc-HRP. Chemiluminescence of Western blot bands was quantitated by using the VersaDoc Imaging System (Model 1000, Bio-Rad) and its software (Quantity One, Version 4.5.1).

The role of LRP6 in PA-mediated toxigenicity was confirmed by multiple lines of evidence: 1) regulation of the toxin resistance phenotype in clone ATR43 by tetracycline (FIG. 1B); 2) reproduction of the toxin resistance phenotype by antisense expression of the Irp6 EST in naïve cells (FIG. 1F); 3) reproduction of the toxin resistance phenotype by siRNA corresponding to sequences in the Irp6 open reading frame (ORF) and reversal of this effect by overexpression of LRP6 protein containing silent mutations that make it non-susceptible to inhibition by the siRNA (FIG. 1J and 1 K); 4) creation of toxin resistance by expression of a dominant negative truncated LRP6 mutant protein lacking the cytoplasmic domain of the protein (FIG. 2H); 5) protection of cells from anthrax toxicity by antibodies directed against epitopes in the LRP6 extracellular domain (FIG. 6); 6) biochemical evidence and deconvolution immunofluorescence microscopy results showing reduced internalization of PA in ATR43 cells and in cells expressing siRNAs directed against lrp6 mRNA (FIG. 2); and 7) our demonstration using both fluorescence microscopy and immunoprecipitation approaches that the LRP6 protein interacts with the PA receptors, TEM8 and CMG2, and controls PA-triggered internalization of the receptors (FIGS. 4-5).

The present discovery of the role of LRP6 in anthrax toxicity and the demonstration that antibodies directed against the extracellular domain of LRP6 protect cells grown in culture against killing by anthrax toxin demonstrates that the immunological targeting of LRP6 will prove useful in protecting against the effects of accumulated toxin during the late stages of anthrax disease when antibacterial methods are no longer of therapeutic value.

The above results and discussion demonstrate that the invention provides important new approaches to preventing and/or treating disease conditions resulting from exposure to *B. anthracis*. A significant advantage of the subject invention is that it is not based on targeting the pathogen itself, but instead to a host receptor. As such, the subject methods find use in the treatment of subjects in the late stage anthrax toxin mediated disease conditions, in which agents targeting the pathogen itself are no longer effective. Accordingly, the subject invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of inhibiting entry of anthrax toxin into a cell, said method comprising:
    contacting a cell exposed to anthrax toxin with an effective amount of an antibody or binding fragment thereof specific for lipoprotein-related receptor protein 6 (LRP6), wherein said antibody or binding fragment thereof inhibits entry of said anthrax toxin into said cell.

2. The method according to claim 1, wherein said anthrax toxin is selected from lethal factor (LF) and edema factor (EF).

3. The method according to claim 1, wherein said antibody or binding fragment thereof inhibits binding of protective antigen (PA) to LRP6.

4. A method of reducing anthrax toxin susceptibility of a cell, said method comprising:
    contacting a cell with an effective amount of an antibody or binding fragment thereof specific for LRP6, wherein said antibody or binding fragment thereof inhibits entry of an anthrax toxin into said cell; and
    exposing said cell to an anthrax toxin;
    wherein anthrax toxin susceptibility of said cell is reduced.

5. The method according to claim 4, wherein said anthrax toxin is selected from LF and EF.

6. The method according to claim 1, wherein said antibody or binding fragment thereof binds to an extracellular and/or transmembrane domain of LRP6.

7. A method of inhibiting an anthrax toxin mediated condition in a host, said method comprising:
    administering to a host having an anthrax toxin mediated condition an effective amount of an antibody or binding fragment thereof specific for LRP6, wherein said antibody or binding fragment thereof inhibits entry of an anthrax toxin into a cell so as to inhibit said anthrax toxin mediated condition in said host.

* * * * *